United States Patent [19]
Von Feldt et al.

[11] Patent Number: 5,837,460
[45] Date of Patent: Nov. 17, 1998

[54] METHODS OF IDENTIFYING BIOLOGICALLY ACTIVE RECEPTOR-BINDING PEPTIDES

[75] Inventors: Joan M. Von Feldt, Wilmington, Del.; Thomas Kieber-Emmons, Newtown Square, Pa.; David B. Weiner, Merion, Pa.; William V. Williams, Havertown, Pa.

[73] Assignees: Trustees of the University of Pennsylvania; The Wistar Institute, both of Philadelphia, Pa.

[21] Appl. No.: 712,212

[22] Filed: Sep. 3, 1996

Related U.S. Application Data

[63] Continuation of Ser. No. 235,404, Apr. 29, 1994, abandoned.
[51] Int. Cl.$^6$ .............................. C12Q 1/68; G01N 33/53
[52] U.S. Cl. .............................. 435/6; 435/7.1; 435/70.1; 435/71.1; 435/71.2; 435/965; 436/547
[58] Field of Search ................................ 435/6, 7.1, 70.1, 435/71.1, 71.2, 965; 436/547; 530/387.3, 387.2

[56] References Cited

U.S. PATENT DOCUMENTS 5,091,513  2/1992  Houston et al. ......................... 530/387

FOREIGN PATENT DOCUMENTS

WO 92/19759  11/1992  WIPO .

OTHER PUBLICATIONS

Carson, D. et al, eds., "Idiotypes in Biology and Medicine", Karger Publishers, Basel, 1990, pp. 185–208.
Cantrell, M. et al., "Cloning, Sequence, and Expression of a Human Granulocyte–Macrophage Colony–stimulating Factor", *PNAS USA* 1985, 82, 6250–6254.
Weigert, M. et al., "Rearrangement of Genetic Information May Produce Immunoglobulin Diversity", *Nature* 1978, 276, 785–90.
Williams et al, Structure and Regulation of Internal Image Idiotypes in: Idiotypes in Biology and Medicine Chem. Immunol. Basel, Karger 1990 vol. 48 pp. 185–208.
Williams et al, Design of Bioactive Peptides Based on Antibody–Hypervariable Region Structures, vol. 266 No. 8 pp. 1582–1590, Mar. 15, 1991.
Abbas et al, Cellular and Molecular Immunology, Phildelphia, W.B. Saunders Company pp. 45–46, ©1991.
Balaji et al., *Biologically Active Peptides: Design, synthesis and utilization Vol. 1:* Ch. 2, 35–54 (Edited by Williams and Weiner Technomic Publishing Co., Lancaster) (1992).
Barbas et al., "Assembly of Combinatorial Antibody Libraries on Phage Surfaces: The Gene III Site", *Proc. Natl. Acad. Sci. USA 88:* 7978–7982 (1991).
Barbas et al., "Semisynthetic Combinatorial Antibody Libraries: A Chemical Solution to the Diversity Problem", *Proc. Natl. Acad. Sci. USA 89:* 4457–4461 (1992).

Barbas et al., "Human Monoclonal Fab Fragments Derived from a Combinatorial Library Bind to Respiratory Syncytial Virus F Glycoprotein and Neutralize Infectivity", *Proc. Natl. Acad. Sci. USA 89:*10164–10168 (1992).
Borofsky et al., "Effects of Polyunsaturated Fatty Acids on Interleukin–2–Dependent T Cell Growth", *Immunol. Res. 11:* 154–164 (1992).
Brandhuber et al., "Three–Dimensional Structure of Interleukin–2", *Science 238:* 1707–1709 (1987).
Brown et al., "Two Neutralizing Monoclonal Antibodies Against Human Granulocyte–Macrophage Colony–Stimulating Factor Recognize The Receptor Binding Domain of the Molecule", *J. Immunology 144:* 2184–2189 (1990).
Bruck et al., "Nucleic Acid Sequence of an Internal Image–Bearing Monoclonal Anti–Idiotype and Its Comparison to the Sequence of the External Antigen", *Proc. Natl. Acad. Sci. USA 83: 6578–6582* (1986).
Burton et al., "A Large Array of Human Monoclonal Antibodies to Type 1 Human Immunodeficiency Virus from Combinatorial Libraries of Asymptomatic Seropositive Individuals", *Proc. Natl. Acad. Sci. USA 88:* 10134–10137 (1991).
Cardwell and Rome, "RGD–Containing Peptides Inhibit the Synthesis of Myelin–like Membrane by Cultured Oligodendrocytes", *J. Cell. Biol. 107:* 1551–1559 (1988).
De Vos et al., "Human Growth Hormone and Extracellular Domain of its Receptor: Crystal Structure of the Complex" *Science 255:* 306–312 (1992).
Garrett et al., "Determination of the Secondary Structure and Folding Topology of Human Interleukin–4 Using Three–Dimensional Heteronuclear Magnetic Resonance Spectroscopy", *Biochemistry 31:* 4347–4353 (1992).
Graf et al., "A Pentapeptide from the Laminin B1 Chain Mediates Cell Adhesion and Binds the 67 000 Laminin Receptor", *Biochemistry 26:* 6896–6900 (1987).
Huse et al., "Generation of a Large Combinatorial Library of the Imunoglobulin Repertoire in Phage Lambda", *Science 246:* 1275–1281 (1989).
Iwamoto et al., "YIGSR, A Synthetic Laminin Pentapeptide, Inhibits Experimental Metastasis Formation", *Science 238:* 1132–1134 (1987).
Kabat et al., "Sequences of Proteins of Immunological Interest" published by U.S. Department of Health and Human Services in Bethesda, MD p. 2597 (1991).

(List continued on next page.)

*Primary Examiner*—Marianne P. Allen
*Assistant Examiner*—Patricia A. Duffy
*Attorney, Agent, or Firm*—Woodcock Washburn Kurtz Mackiewicz & Norris LLP

[57] ABSTRACT

A method of identifying peptides which mimic biologically active proteins is disclosed. The method comprises the steps of making a recombinant antibody library from genetic material obtained from an animal which has been immunized against antibodies that bind to the biological active protein to the mimicked. Recombinant antibodies are screened to identify antibodies which compete with the biological active protein. Peptides which comprise the recombinant antibody's CDR sequences are synthesized. Synthetic peptides which mimic GM-CSF are also disclosed.

13 Claims, 11 Drawing Sheets

OTHER PUBLICATIONS

Kieber–Emmons, *Biologically Active Peptides: Design, Synthesis and Utilization* vol. 1: Ch. 1: 3–34 (Edited by Williams and Weiner Technomic Publishing Co., Lancaster) (1992).

Kleinman et al., "Identification of a Second Sctive Site in Laminin for Promotion of Cell Adhesion and Migration and Inhibition of In Vivo Melanoma Lung Colonization", *Arch. Biochem. Biophys. 272:* 39–45 (1989).

Lei et al., "Characterization of the *Erwinia Carotovora PelB* Gene and Its Product Pectate Lyase", *J. Bacteriol. 169:* 4379–4383 (1987).

Levi et al., "A Complementarity–Determining Region Synthetic Peptide Acts as a Miniantibody and Neutralizes Human Immunodeficiency Virus Type 1 In vitro", *Proc. Natl. Acad. Sci. USA 90:* 4374–4378 (1993).

McCallus et al., "Construction of a Recombinant Bacterial Human CD4 Expression System Producing a Bioactive CD4 Molecule", *Viral Imunol. 5:* 163–172 (1992).

Merrifield, "Solid Phase Synthesis. I. The Synthesis of a Tetrapeptide", *J. Am. Chem. Soc. 15:* 2149–2154 (1963).

Miele et al., "Novel Anti–Inflammatory Peptides from the Region of the Highest Similarity Between Uteroglobin and Lipocortin I", *Nature 335:* 726–730 (1988).

Milburn et al., "A Novel Dimer Configuration Revealed by the Crystal Structure at 2.4 Å Resolution of Human Interleukin–5", *Nature 363:* 172–176 (1993).

Pandit et al., "Three–Dimensional Structure of Dimeric Human Recombinant Macrophage Colony–Stimulating Factors", *Science 258:* 1358–1362 (1992).

Powers et al., "The High–Resolution, Three–Dimensional Solution Structure of Human Interleukin–4 Determined by Multidimensional Heteronuclear Magnetic Resonance Spectroscopy", *Biochemistry 32:* 6744–6762 (1993).

Pride et al., "Molecular Mimicry of Hepatitis B Surface Antigen by an Anti–Idiotype–Derived Synthetic Peptide", *Proc. Natl. Acad. Sci. USA 89:* 11900–11904 (1992).

Redfield et al., "Loop Mobility in a Four–Helix–Bundle Protein: $^{15}$N NMR Relaxation Measurements on Human Interleukin–4" *Biochemistry 31:* 10431–10437 (1992).

Smith et al., "Human Interleukin 4: The Solution Structure of a Four–helix Bundle Protein", *J. Mol. Biol. 224:* 899–904 (1992).

Taub et al., Peptide Sequences from the Hypervariable Regions of Two Monoclonal Anti–idiotypic Antibodies Against the Thyrotropin (TSH) Receptor Are Similar to TSH and Inhibit TSH–Increased cAMP Production in FRTL–5 Thyroid Cells:, *J. Biol. Chem. 267:* 5977–5984 (1992).

Taub et al., "A Monoclonal Antibody Against the Platelet Fibrinogen REceptor Contains a Sequence That Mimics a Receptor Recognition Domain in Fibrinogen" *J. Biol. Chem. 264:* 259–265 (1989).

Von Feldt, *Biologically Active Peptides: Design, Synthesis and Utilization* vol. 1: Ch. 3: 55–86 (Edited by Williams and Weiner Technomic Publishing Co., Lancaster) (1992).

Ward et al., "Binding Activities of a Repertoire of Single Immunoglobulin Variable Domains Secreted in *Escherichia Coli*", *Nature 341:* 544–546 (1989).

Williams et al., "Sequences of the Cell–Attachment Sites of Reovirus Type 3 and Its Anti–Idiotypic/Antireceptor Antibody: Modeling of Their Three–Dimensional Structures", *Proc. Natl. Acad. Sci. USA 85:* 6488–6292 (1988).

Williams et al., "Development of Biologically Active Peptides Based on Antibody Structure", *Proc. Natl. Acad. Sci. USA 86:* 5537–5541 (1989).

Williams et al., "Contact Residues and Predicted Structure of the Reovirus Type 3–Receptor Interaction", *J. Biol. Chem. 266:* 9241–9250 (1991).

Williams et al., "Recombinant Single Chain Human Antibodies to HIV–1 gp160", *Transgene 1:* 113–123 (1993).

Welling et al., "A Ten–Residue Fragment of an Antibody (Mini–Antibody) Directed Against Lysozyme as Ligand in Immunoaffinity Chromatography", *J. of Chromatography 548:* 235–242 (1991).

Altmann et al., "Single Proline Substitutions in Predicted α–Helices of Murine Granulocyte–Macrophage Colony–Stimulating Factor Result in a Loss in Bioactivity and Altered Glycosylation", *J. Biol. Chem. 266:* 5333–5341 (1991).

Clark–Lewis et al., "Structure–Function Studies of Human Granulocyte–Macrophage Colony–Stimulating Factor", *J. Immunology141:* 881–889 (1988).

Diederichs et al., "Novel Fold and Putative Receptor Binding Site of Granulocyte–Macrophage Colony–Stimulating Factor", *Science 254:* 1779–1782 (1991).

Diederichs et al., "Low–Resolution Structure of Recombinant Human Granulocyte–Macrophage Colony Stimulating Factor", *J. Mol. Biol. 221:*55–60 (1991).

Dorssers et al., "Receptor and Antibody Interactions of Human Interleukin–3 Characterized by Mutational Analysis", *J. Biol. Chem. 266:* 21310–21317 (1991).

Kanakura et al., "Identification of Functionally Distinct Domains of Human Granulocyte–Macrophage Colony–Stimulating Factor Using Monoclonal Antibodies", *Blood 77:* 1033–1043 (1991).

Shannon et al., "Nuclear Proteins Interacting With the Promoter Region of the Human Granulocyte/Macrophage Colony–Stimulating Factor Gene" *Proc. Natl. Acad. Sci. USA 85:* 674–678 (1989).

Kieber–Emmons et al., "Biological Characteristics of an HIV–1 Envelope–Derived Synthetic Peptide" *Vaccines 90*(Cold Spring Harbor): 321–326 (1990).

Kieber–Emmons and Kohler, "Evolutionary Origin of Autoreactive Determinants (Autogens)", *Pro. Natl. Acad. Sci. USA 83:* 2521–2525 (1986).

Kieber–Emmons et al., "Structural Considerations in Idiotypic Vaccine Design" *Monogr. Allergy. 22:* 126–133 (1987).

Lokker et al., "Structure–Activity Relationship Study of Human Interleukin–3", *J. Biol. Chem. 255:* 10624–10631.

Lopez et al., "Residue 21 of Human Granulocyte–Macrophage Colony–Stimulating Factor is Critical for Biological Activity and For High but Not Low Affinity Binding", *Embo. J. 11:* 909–916 (1992).

Nice et al., "Human Granulocyte–Macrophage Colony–Stimulating Factor (hGM–CSF): Identification of a Binding Site for a Neutralizing Antibody" *Growth Factors 3:* 159–169 (1990).

Shanafelt and Kastelein, "High Affinity Ligand Binding is not Essential for Granulocyte–Macrophage Colony–Stimulating Factor Receptor Activation", *J. Biol. Chem. 267:* 25466–25472 (1992).

Shanafelt et al., "The Amino–Terminal Helix of GM–CSF and IL–5 Governs High Affinity Binding to Their Receptors", *Embo. J. 10:* 4105–4112 (1991).

Shanafelt and Kastelein, "Identification of Critical Regions in Mouse Granulocyte–Macrophage Colony–Stimulating Factor by Scanning–Deletion Analysis", *Proc. Natl. Acad. Sci. USA 86*: 4872–4876 (1989).

VonFeldt et al., "Molecular Structure and Granulocyte/Macrophage Colony–Stimulating Factor Activity", *DNA Cell Biol 3*: 183–191 (1992).

Williams et al., "Immune Response to a Molecularly Defined Internal Image Idiotope", *J. Immunol. 142*: 4392–440 (1989).

Williams et al., "Modulation of T Cell Responses with MHC–Derived Peptides", *Immunol. Res. 11*: 11–23 (1992).

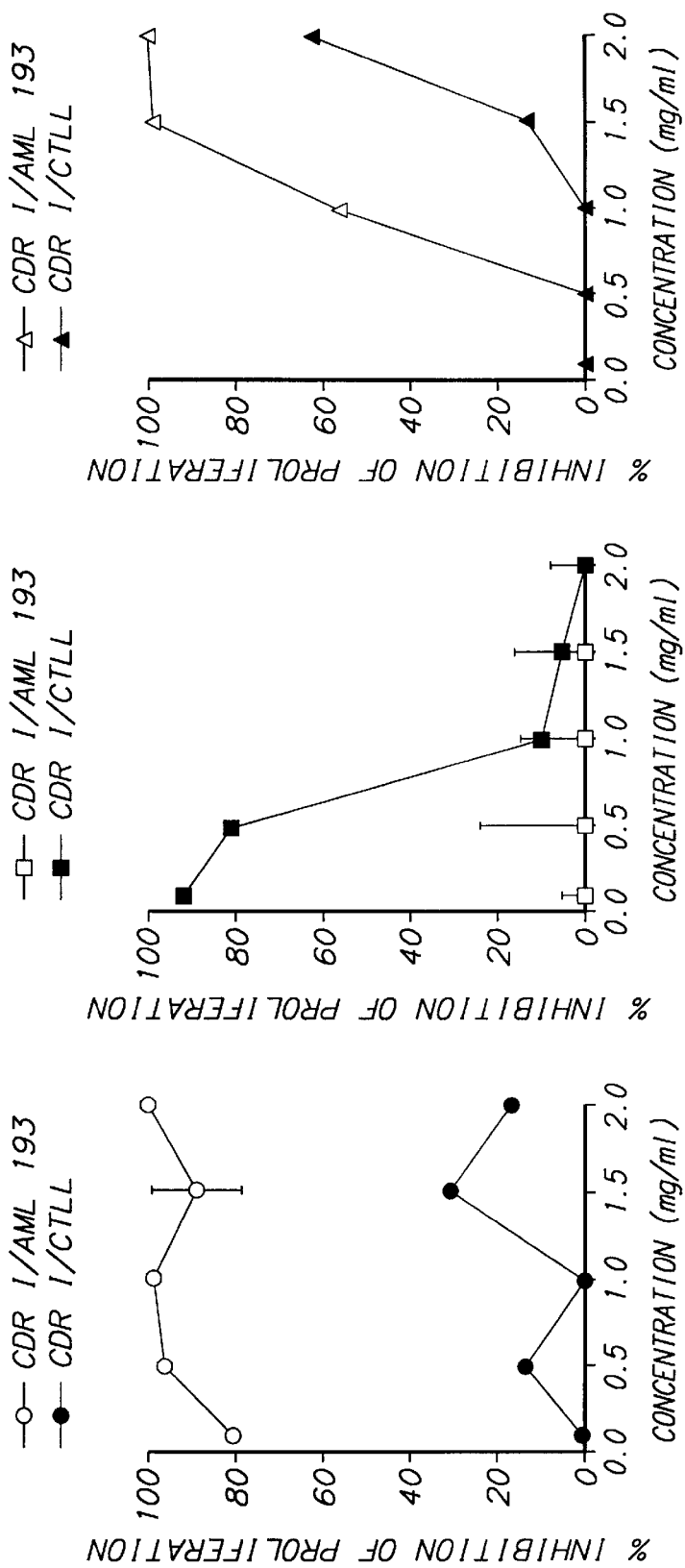

METHODS OF IDENTIFYING BIOLOGICALLY ACTIVE RECEPTOR-BINDING PEPTIDES

This is a continuation of application Ser. No. 08/235,404, filed Apr. 29, 1994 now abandoned.

FIELD OF THE INVENTION

The present invention relates to methods of identifying small peptides which mimic biologically active compounds and to such small peptides.

BACKGROUND OF THE INVENTION

Development of small molecular mimics of larger, polypeptide ligands is one approach to pharmacophore design. Several strategies are available for the development of such mimics, including the use of small oligopeptide analogs derived from native sequence (Miele, et al. (1988) *Nature* 335, 726–730; Graf, et al. (1987) *Biochemistry* 26, 6896–6900; Cardwell, et al., (1988) *J Cell Biol* 107, 1551–1559; Iwamoto, et al., (1987) *Science* 238, 1132–1134 and Kleinman, et al., (1989) *Arch Biochem Biophys* 272, 39–45; each which is incorporated herein by reference.) development of peptidic and non-peptidic analogs based on molecular structure data (Kieber-Emmons, T. (1992) *Biologically active peptides: Design, synthesis and utilization* (Lancaster, Pa.) 1, 3–34; and Balaji, et al., (1992) *Biologically active peptides: Design, synthesis and utilization* (Lancaster, Pa.) 1, 35–54, each of which is incorporated herein by reference.) and analysis of alternative ligands (Von Feldt, et al. (1992) *Biologically active peptides: Design, synthesis and utilization* (Lancaster, Pa.) 1, 55–86, which is incorporated herein by reference.). Alternative ligands that bind to the same site as the native ligand provide the opportunity to investigate structural and chemical constraints for binding in the setting of diverse backbone geometries. This has the potential to identify critical contact residues based on similar structural and chemical characteristics between the diverse ligands.

Prior studies have investigated a monoclonal antibody (mAb), 87.92.6, which mimicked a neutralizing epitope on the reovirus type 3 neutralizing mAb and the reovirus type 3 receptor. Sequence similarity between 87.92.6 light chain second complementarily determining region (CDR II) and the reovirus type 3 hemagglutinin (Bruck, et al. (1986) *Proc Natl Acad Sci USA* 83, 6578–6582, which is incorporated herein by reference) allowed the development of synthetic peptides and peptidomimetics which bound both the neutralizing mAb and the reovirus type 3 receptor. These peptides and peptidomimetics also demonstrated biological activity on reovirus type 3 receptor bearing cells. The use of anti-receptor mAbs as a source of sequence/structural information to aid in peptide design has allowed the development of similar biologically active peptides in several systems, including the platelet fibrinogen receptor (Taub, et al. (1989) *J Biol Chem* 264, 259–265, which is incorporated herein by reference), the thyroid stimulating hormone receptor (Taub, et al. (1992) *J Biol Chem* 267, 5977–84, which is incorporated herein by reference), and epitopes on the human immunodeficiency virus (Levi, et al. (1993) *Proc Natl Acad Sci USA* 90, 4374–8, which is incorporated herein by reference) and hepatitis B surface antigen (Pride, et al. (1992) *Proc Natl Acad Sci USA* 89, 11900–4, which is incorporated herein by reference).

Recombinant antibodies have been developed which are expressed in bacteria (Ward, et al. (1989) *Nature* 341, 544–546 and Huse, et al. (1989) *Science* 246, 1275–1281, each of which is incorporated herein by reference.) or on the surface of filamentous bacteriophage (Barbas, et al. (1992) *Proc Natl Acad Sci USA* 89, 10164–8; Burton, et al. (1991) *Proc Natl Acad Sci USA* 88, 10134–7; Barbas, et al. (1992) *Proc Natl Acad Sci USA* 89, 4457–61; and Barbas, et al. (1991) *Proc Natl Acad Sci USA* 88, 7978–82, each of which is incorporated herein by reference). The advantages of recombinant approaches to antibody development include the ability to rapidly screen thousands of clones simultaneously, the potential to detect binding moieties poorly represented in the initial repertoire, and the potential to express isolated variable regions.

There is a need for additional, more efficient methods of identifying small peptides which mimic biologically active compounds. There is a need for small peptides which mimic biologically active compounds.

SUMMARY OF THE INVENTION

The present invention relates to methods of identifying peptides that have 5–30 amino acids which mimic biologically active proteins. The methods of the invention comprise the steps of:

1) inoculating a first animal with an amount of a biologically active protein sufficient to invoke an immune response which includes antibody production by the first animal against the biologically active protein;
2) isolating antibodies from the first animal;
3) inoculating a second animal with an amount of the isolated antibodies sufficient to invoke an immune response which includes antibody production by the second animal against the anti-biologically active protein antibodies;
4) isolating RNA from spleen cells from the second animal and generating CDNA from such RNA;
5) inserting the CDNA into an expression vector to form recombinant expression vectors and introducing the recombinant expression vectors into suitable host cells to produce transformed host cells which express the CDNA and produce proteins encoded thereby;
6) identifying proteins which are recombinant antibodies, which bind to monoclonal antibodies specific for the biologically active protein and which compete with biological active protein to bind with monoclonal antibodies specific for the biologically active protein;
7) identifying amino acid sequence of complementarity determining regions of the recombinant antibodies; and
8) synthesizing peptides with amino acid sequence that consist of between 5–30 amino acid residues and which comprise the identified amino acid sequence.

The present invention relates to synthetic peptides which mimic GM-CSF.

BRIEF DESCRIPTION OF THE FIGURES

FIG. 1 shows data from experiments evaluating the biological activity of antisera. Proliferation of the human GM-CSF dependent cell line MO7E was performed as noted in Materials and Methods in the presence of varying dilutions of murine anti-GM-CSF (following the fifth boost) and murine anti-anti-GM-CSF (following the ninth boost). Counts per minute incorporated ± the standard deviation of triplicate wells is shown for various dilutions of antisera. In similar experiments, the inhibition induced by anti-GM-CSF titered out at 1:20,000 to 1:100,000 dilutions.

FIG. 2 shows the relative location of PCR primers and probes.

FIG. 3A–3E show data from library screening. Photo 3A is a photo from the first round library screening was carried out on 30 filters lifted from 30 LB/amp plates representing a total of ~15,000–20,000 colonies. A representative filter is shown here. Photo 3B is a photo from the second round screening of one positive clone (clone 23.2) replated and probed with $^{125}$I-126.213. Compare with Photo 3C is a photo from the second round screening of a control clone with an irrelevant $V_L$ region. Photo 3D is a photo form the third round screening of clone 23.2. Compare with Photo 3E which is a photo of *E. coli* transformed with $pDAB_L$ alone.

FIGS. 4A–4D show data generated from the characterization of rAb $V_L$ Regions. Panel 4A is the data from a Western blot analysis of rAb fragments. *E. coli* transformed with various plasmids were induced or left uninduced, lysates prepared, and Western blotting performed with 126.213 as the primary antibody as noted in Materials and Methods. Lanes were as follows: 1) clone 23.2 uninduced; 2) clone 23.2 induced; 3) clone 5.1 uninduced; 4) clone 5.1 induced; 5) $pDAB_L$ alone uninduced; 6) $pDAB_L$ alone induced; 7) 300 ng GM-CSF (positive control). Molecular weight markers are indicated. The arrow indicates the band specifically induced. Panels 4B and 4C show data from inhibition of immunoprecipitation by 23.2. Immunoprecipitation of $^{125}$I-GM-CSF was performed as noted in Materials and Methods section in Example 1. Lysates of *E. coli* expressing 23.2 or control (irrelevant clone) were prepared, protein quantified, and 400 $\mu$g used to inhibit immunoprecipitation. In Panel 4B, inhibitors were added as follows: 1) $pDAB_L$ alone induced; 2) 300 ng GM-CSF; 3) clone 25.1 uninduced; 4) clone 25.1 induced; 5) clone 23.2 uninduced; 6) clone 23.2 induced; 7) $^{14}$C-molecular weight markers. Panel 4C shows data from the same experiment as in Panel 4B, with counts per minute bound plotted for the various inhibitors. Percent Inhibition of binding was determined by the formula:

$$\% \text{ Inhibition} = 100 \times \frac{\text{Maximum } CPM \text{ bound} - \text{Experimental } CPM \text{ Bound}}{\text{Maximum } CPM \text{ bound}}$$

The mean± standard deviation of replicate determinations is shown. In Panel 4D, the autoradiograph shown at the top of the panel and the quantification shown at the bottom of the panel show data from inhibition of immunoprecipitation by 23.2. This was as for data in Panels 4B and 4C, comparing increasing amounts of induced lysate for their ability to inhibit 126.213 immunoprecipitation of GM-CSF. Increasing amounts of lysate were added to immunoprecipitation reactions with 126.213 coated beads prior to addition of $^{125}$I-GM-CSF. Lanes were as follows: (1) positive control (no inhibitor). (2) 300 ng unlabeled GM-CSF. (3–5) control lysate versus (6–8) 23.2 lysate added as 100 $\mu$g (3& 6), 200 $\mu$g (4&7), or 400 $\mu$g (5&8) protein equivalent. The relative inhibition of immunoprecipitation was determined by densitometry.

FIG. 5 shows inhibition of $^{125}$I-GM-CSF binding to HL-60 cells by 23.2. The binding assay was performed as noted in Materials and Methods, in the presence or absence of increasing amounts of 23.2 or control (pUC18) lysates. The counts per minute (CPM) bound±standard error of replicate determinations for two lysate preparations is shown.

FIGS. 6A–6F show results from studies of binding of 126.213 to synthetic peptides derived from the GM-CSF sequence. Binding was performed by ELISA assay as described in Materials and Methods in Example 1. The values shown are OD490 nm binding to the peptides at the concentration noted minus OD490 nm binding to BSA coated control plates. The mean±SD of triplicate wells is shown for increasing amounts of purified 126.213 added. (Panel 6A) Binding to pep4. (Panel 6B) Binding to p29. (Panel 6C) Binding to pep5. (Panel 6D) Binding to pep3. (Panel 6E) Binding to p28. (Panel 6F) Binding to pep6.

FIG. 7 shows results of inhibition of $^{125}$I-GM-CSF binding to HL-60 cells by peptides. The binding assay was performed as noted in Materials and Methods of Example 1, in the presence or absence of increasing amounts of peptides as noted. The mean of replicate determinations is shown, with % inhibition calculated as noted in above description of FIG. 4.

FIGS. 9A–9C show results of studies to assess the ability of each CDR-derived peptide described in Example 2 to inhibit proliferation of specific cells at various concentrations.

Figure 1:
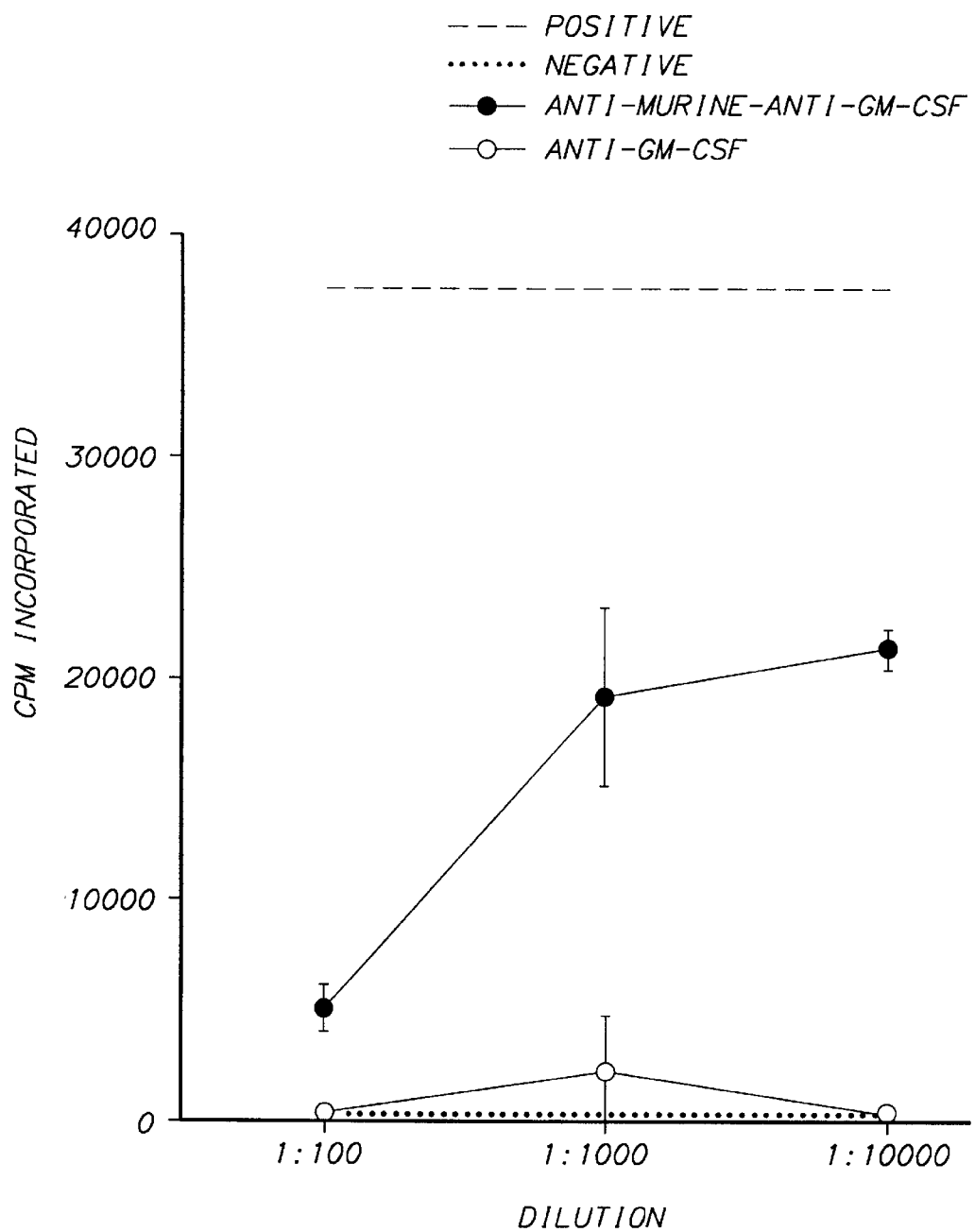

DETAILED DESCRIPTION OF THE INVENTION

As used herein, the term "mimic" is meant to refer to binding to the same molecules. Accordingly, peptides which mimic proteins bind to the same molecules as the proteins do. The peptides that mimic proteins may exhibit the same biological activity as the protein and thus be an agonist. Alternatively, the peptides that mimic proteins may bind to the same molecule but not exhibit the same biological activity as the protein, thereby blocking the binding by the protein and thus being an antagonist.

As used herein, the term "suitable host cell" is meant to refer to a host cell which is compatible with an expression vector, that is the expression vector may be maintained by and function in the host cell.

According to one aspect of the present invention, an efficient method is provided for identifying synthetic peptides which mimic biologically active proteins. Since peptides which mimic biologically active proteins may themselves be biologically active or inactive, the present invention is useful to find relatively small peptides which can either be administered in place of proteins or to counteract the effects of such proteins. The advantages of small peptide agonists over biologically active proteins are many. Small peptides are less immunogenic and easier and cheaper to manufacture. Small peptide antagonists share these advantages and are useful to alleviate the negative effects caused by some biologically active proteins in certain diseases conditions and disorders. Since peptides which mimic biologically active proteins have the same binding specificity as the biologically active protein, the peptides may be used as a reagent in place of the protein in binding assays such as diagnostic and laboratory immunoassays.

According to the methods of the invention, the synthetic peptides are designed based upon the complementarity determining regions (CDRs) of recombinant antibodies (rABs) which are produced from genetic material derived from spleen cells of animals in which an antibody reaction is induced against antibodies specific for the biologically active protein. The CDRs of the rABs thus include anti-idiotype CDRs which resemble at some level, the biologically active protein. While the synthetic peptides thus produced and the CDRs upon which they are designed are reverse turns, the methods of the present invention can be used to identify synthetic peptides which mimic biologically active proteins which are composed of helical structures. Thus, the present invention provides the unexpected advantage of being applicable to design of synthetic peptides with reverse turn structures which bind to molecules in the same manner in which helical structures of biologically active proteins do.

Essentially, antibodies are generated against the biologically active protein to be mimicked. The antibodies are then used as antigens to generate antibodies against the antibodies; some of the anti-antibodies having binding regions which mimic the biologically active protein. One an animal is confirmed to make anti-antibodies, a recombinant antibody library is generated using genetic material derived from the animal's spleen cells. The recombinant antibody library is then screened to identify a recombinant antibody which has a binding regions which mimic the biologically active protein. Such a recombinant antibody will compete with the biologically active protein such as in binding to monoclonal antibodies (MAbs) which specifically bind to the biologically active protein. Using the recombinant antibody library, one the recombinant antibody which has a binding regions which mimic the biologically active protein is identified, the amino acid sequence of the CDRs may be ascertained and that information is then used to synthesize small peptides which mimic the biologically active protein.

The biologically active proteins may include any protein which interacts with another protein including but not limited to: classes 1 and 2 major histocompatibility complexes; receptors; receptor ligands such as cytokines and growth factors; enzymes; adhesion molecules; and antibodies. The biologically active proteins include those in which the active regions, i.e. the portion of the biologically active protein which directly interacts with another molecule, are reverse turns, helices or sheets. In some preferred embodiments, the active regions of the biologically active proteins are helices. In some preferred embodiments, the biologically active proteins are selected from the group consisting of members of the four- helix bundle family of cytokines and growth factors. In some preferred embodiments, the biologically active proteins are selected from the group consisting of: GM-CSF, IL-3, IL-5, growth hormone, M-CSF, G-CSF and IL-2.

The methods of the present invention provide the step of generating antibodies against the biologically active protein which is to be mimicked. The means to produce such antibodies are well known to those having ordinary skill in the art. Briefly, an animal is administered sufficient amounts of the protein to induce an antibody response by the animal. Multiple administrations may be necessary or desirable to induce a high titer antibody response. The sera of the animal may be evaluated to confirm that antibodies are being produced against the biologically active protein. One having ordinary skill in the art can readily perform the evaluation using well known assays such as immunoassays or biological activity assays such as neutralizing assays.

The first animal may be any immunocompetent animal capable of generating antibodies against the biologically active protein. The first animal is preferably a mammal; more preferably a laboratory animal such as a mouse, rat, hamster, guinea pig or rabbit. In some preferred embodiments, the first animal is a mouse.

The anti-biologically active protein antibodies are isolated from the first animal using standard techniques well known to those having ordinary skill in the art. In some embodiments, the anti-biologically active protein antibodies are anti-biologically active protein IgG antibodies isolated from sera from said first animal by affinity chromatography with sepharose-protein A.

The methods of the present invention provide the step of generating antibodies against the anti-biologically active protein antibodies. The means to produce such anti-antibody antibodies are well known to those having ordinary skill in the art. Briefly, an animal is administered sufficient amounts of the antibodies to induce an antibody response by the animal against the antibodies. Multiple administrations are desirable and often necessary to induce a high titer antibody response. The sera of the animal may be evaluated to confirm that antibodies are being produced against the anti-biologically active protein antibodies. One having ordinary skill in the art can readily perform the evaluation using well known assays such as biological activity assays such as neutralizing assays.

The second animal may be any immunocompetent animal capable of generating antibodies against the anti-biologically active protein antibodies. The second animal is preferably a mammal; more preferably a laboratory animal such as a mouse, rat, hamster, guinea pig or rabbit. The second animal is preferably the same species as the first animal. In some preferred embodiments, the second animal is a mouse. In preferred embodiments, the first animal is a mouse and the second animal is a mouse.

After the second animal produces antibodies specific for the anti-biologically active protein antibodies, the animal is sacrificed and the genetic material form the animal's spleen is used to produce a recombinant antibody library. Typically, using well known techniques, the RNA is extracted from spleen cells and used to generate cDNA. Among the RNA and therefore the cDNA is that which encodes antibodies that specifically bind to the anti-biologically active protein antibodies.

The cDNA may be inserted directly into vectors for preparing the library. Alternatively, the cDNA may be used as a starting material to further isolate and/or amplify the genetic material that encodes antibodies, portions thereof or fragments of such portions.

In preferred embodiments, polymerase chain reaction (PCR) techniques are performed to amplify the DNA sequences in the cDNA which encode antibody light chains only. Similarly, PCR techniques may be performed to amplify the DNA sequences in the cDNA which encode antibody heavy chains only or both light chains and heavy chains. Likewise, PCR techniques may be performed to amplify the DNA sequences in the cDNA which encode fragments of antibody lights chains only or fragments of heavy chains only or fragments of both light chains and heavy chains. It is only necessary that portion of the antibodies which include the CDRs be cloned. The techniques for amplifying these DNA sequences are routine and the sequence information necessary to design primers useful to accomplish such amplification is well known and can be practiced by those having ordinary skill in the art routinely.

Whether the cDNA is inserted into an expression vector or an amplified sequence derived from the cDNA is inserted into an expression vector, the resulting recombinant expression vectors which are formed are used to transform suitable host cells which can express the inserted DNA and produce the protein encoded thereby.

Recombinant expression vectors are well known and many commercially available vectors may be used. It is preferred that the expression vector used provide a signal sequence to the inserted protein to allow secretion upon production of the protein. Generally, the protein is produced with a signal sequence which directs the transportation of the protein and which is clipped off the protein upon secretion. According to the preferred embodiment, the recombinant expression vector used is plasmid pDAB$_L$ (which is described in U.S. patent application Ser. No. 07/909,295; McCallus, et al. (1992) *Viral Immunol* 5, 163–172; and Williams, et al. (1993) *Transgene* (in press); each of which are incorporated herein by reference). A suitable host cell is one in which the expression vector is functional. In the preferred embodiment, the host cell is *E. coli*. Transformation of a host cell with a recombinant expression vector is routine.

According to a preferred embodiment, the host cell is *E. coli* and the library generated by transformation of the *E. coli* with the recombinant vector is grown as individual colonies on agar plates. Using nitrocellulose paper or a similar solid substrate, multiple identical copies of the library may be lifted and grown simultaneously. Colony lifting is well known as are the concept and techniques for evaluating multiple identical copies of a library.

The transformed host cells are maintained under conditions which allow for expression of the inserted DNA. In a preferred embodiment, the inserted DNA is under the regulatory control of the β-galactosidase promoter in the expression vector. Accordingly, addition of isopropylthiogalactosidase is required to induce expression of the insert.

According to a preferred embodiment, the host cell is *E. coli* and the library generated by transformation of the *E. coli* with the recombinant vector is grown as individual colonies on agar plates. Using nitrocellulose paper or a similar solid substrate, multiple identical copies of the library may be lifted and grown simultaneously. Colony lifting is well known as are the concept and techniques for evaluating multiple identical copies of a library.

The protein produced by expression of the inserts in the recombinant expression vectors may then be screened to identify the recombinant antibodies which compete with antibodies against the biologically active protein. The assays performed to determine these properties may be routinely performed by those having ordinary skill in the art.

The protein produced by expression of the inserts in the recombinant expression vectors may then be screened to identify the recombinant antibodies which bind to antibodies against the biologically active protein. In a preferred embodiment, an anti-biologically active protein MAb is used to identify the recombinant antibodies which bind to antibodies against the biologically active protein.

As an additional preferred step, any recombinant antibody identified as binding to the anti-biologically active protein MAb is screen to determine if it binds to an unrelated antibody of the same isotype as the anti-biologically active protein MAb. This ensures that the recombinant antibody is not binding to the constant region of the anti-biologically active protein MAb. Thus, for example, if the anti-biologically active protein MAb is an IgM, an unrelated IgM is used to confirm that the recombinant antibodies which bind to the anti- biologically active protein MAb do not bind to any IgM.

Once the recombinant antibodies are identified which bind to the anti-biologically active protein MAb, additional routine assays may be performed to determine if the recombinant antibodies complete with the biologically active protein to bind to the anti-biologically active protein MAb. These assays will ensure that the recombinant antibody is binding to the MAb at the same site as the biologically active protein and thus that the recombinant antibodies, or more accurately the CDRs of the recombinant antibodies, mimic the biologically active protein.

Upon identifying recombinant antibodies that compete with biologically active protein to bind to anti-biologically active protein MAb, the sequences of the CDRs of such recombinant antibodies are determined. In preferred embodiments, the recombinant antibody library is an *E. coli* library and the clones identified as encoding recombinant antibodies that compete with biologically active protein to bind to anti-biologically active protein MAb may be grown up in large quantities. Using well known techniques, the DNA sequence that encodes the CDRs is determined and thus the amino acid sequence of the CDRs is determined.

Peptides are synthesized with amino acid sequence that consist of between 5–30 amino acid residues and which comprise the amino acid sequence of the CDRs. In some embodiments, peptides have amino acid sequences that consist of between 10–25 amino acid residues. In some embodiments, peptides have amino acid sequences that consist of between 15–22 amino acid residues. In some preferred embodiments, peptides have amino acid sequences that consist of 17, 18, 19, 20 or 21 amino acid residues. Generally, the entire CDR sequence identified is incorporated into the synthetic peptide. In addition, in some embodiments, it is preferred if some of the adjacent framework sequence are also provided to help facilitate the reverse turn conformation characteristic of CDRs. Generally, multiple hydrophobic residues which are adjacent to the CDR, tryptophan residues and multiple cysteine residues other than those which may be at the N- or C-terminal position are not included. Peptides may be synthesized using standard solid phase peptide synthesis methods. Peptides of the invention may be prepared using the solid-phase synthetic technique. Synthetic peptides may be routinely tested to ensure they mimic the biologically active protein.

In some embodiments, the synthetic peptide is provided as a dimer, either a homodimer or as a heterodimer associated with another peptide. In some embodiments, the synthetic peptide is conformationally restricted such as by cyclization using disulfide bonds between N-terminal and C-terminal cysteine residues.

According to another aspect of the present invention, synthetic peptides which mimic GM-CSF are provided. Such peptides were identified following the methods of the present invention. Example 1 reports the identification of peptides which mimic GM-CSF. Example 2 reports data generated showing that the peptides mimic GM-CSF and studying the activity of the peptides. Example 3 disclosed peptides GM-CSF antagonists which were identified by other methods.

The synthetic peptides of the invention may be 5–30 amino acids, preferably 15–25 amino acids, more preferably 19–23 amino acids. Fragments of SEQ ID NOS:1–4 which mimic GM-CSF are contemplated as are peptides which comprise one of SEQ ID NOS:1–4 or a fragment thereof in combination with other amino acid sequences. Further, it is contemplated that peptides consisting of 5–30 amino acid residues may comprise amino acid sequence essentially identical to one of SEQ ID NOS:1–4 or a fragment thereof but with substitutions, deletions or insertions of one or more amino acid residues.

The synthetic peptides of the invention disclosed in Example 2 are SEQ ID NO:1 and SEQ ID NO:2. The synthetic peptides of the invention disclosed in Example 3 are SEQ ID NO:3 and SEQ ID NO:4.

| |
|---|
| SEQ ID NO:1 is:<br>Cys Arg Ala Ser Lys Ser Val Ser Ser Ser Gly Tyr Ser<br>Tyr Met His Trp Tyr Gln Gln<br>SEQ ID NO:2 is:<br>Cys Gln His Ser Arg Glu Leu Pro Trp Thr Phe Gly Gly<br>Gly Thr Arg Leu Glu Ile Lys Arg<br>SEQ ID NO:3 is:<br>Cys Asn Ala Ile Gln Glu Ala Arg Arg Leu Leu Asn Leu<br>Ser Arg Asp<br>SEQ ID NO:4 is:<br>Cys Leu Gln Thr Arg Leu Glu Leu Tyr Lys Gln Gly Leu<br>Arg Glu Ser Leu Thr Lys Gly Pro Leu Thr. |

SEQ ID NO:3 binds to the β chain of the GM-CSF receptor. SEQ ID NO:1, SEQ ID NO:2 and SEQ ID NO:4 bind to the α chain. Each peptide when acts as an antagonist when delivered alone. However, combinations of SEQ ID NO:3 with any of the α chain binding peptides may be useful as GM-CSF agonist peptides.

The synthetic peptides of the invention which mimic GM-CSF may be used as reagents in place of GM-CSF in binding assays such as diagnostic and laboratory immunoassays. In assays which use anti-GM-CSF antibodies to detect and/or quantitate levels of GM-CSF in a test sample, samples containing known quantities of GM-CSF are used as controls (control samples) or as competitive binders in competition binding assays. Synthetic peptides of the invention may be used in place of control samples or competitive binders in such assays.

Agonist combinations of the peptides (SEQ ID NO:3+SEQ ID NO:1, SEQ ID NO:3+SEQ ID NO:2 and SEQ ID NO:3+SEQ ID NO:4) may be useful as therapeutics in applications when GM-CSF can be administered, specifically those which exhibit aganosist activity. Such applications include administration of peptides as upregulators in the production of cells of the immune system such as administration to individuals undergoing chemotherapy to induce replacement of destroyed cells.

Administration of the peptides in their antagonist form make themm useful as anti-inflammatory agents. In one preferred embodiment, the peptides are provided as GM-CSF antagonists in eye drops for alleviation of ocular inflammation. Other inflammatory diseases include autoimmune diseases. Auto immune diseases generally refer to those diseases involving a self-directed immune response. Autoimmune diseases are referred to as being B cell mediated or T cell mediated. T cell mediated autoimmune diseases include Rheumatoid arthritis (RA), multiple sclerosis (MS), Sjogrens, sarcoidosis, insulin dependent diabetes mellitus (IDDM), autoimmune thyroiditis, reactive arthritis, ankylosing sponduilitis, scleroderma, paymyositis, dermatomyositis, psorisis, vasculitis, Wegner's granulomatosis, Crohn's disease and colitis. Each of these diseases is characterized by high affinity T cell receptors that bind to endogenous antigens and initiate the inflammatory cascade associated with autoimmune diseases. B cell mediated autoimmune diseases include Lupus (SLE), Grave's disease, myathon, myasthinia gravas, autoimmune hemolytic anemia, autoimmune thrombocytopenia, asthma, cryobulinemia, primary biliary sclerosis and pernias anemia. Each of these diseases is characterized by antibodies which bind to endogenous antigens and initiate the inflammatory cascade associated with autoimmune diseases.

The peptides are made by any standard technique. Peptides of the invention are preferably prepared using the solid-phase synthetic technique initially described by Merrifield, in *J. Am. Chem. Soc.,* 15:2149–2154 (1963) which is well known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference.

Peptides of the invention may be provided for pharmaceutical uses as pharmaceutical compositions that comprise the peptides in combination with a pharmaceutically acceptable carrier. The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results. Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

For parenteral administration, the peptides can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives) . The formulation is sterilized by commonly used techniques. Suitable pharmaceutical carriers are described in the most recent edition of *Remington's Pharmaceutical Sciences*, A. Osol, a standard reference text in this field.

EXAMPLES

Example 1

We have developed a recombinant $V_L$ library in *E. coli* derived from mice immunized with polyclonal anti-GM-CSF. This library was screened with a previously described neutralizing anti-GM-CSF mAb 126.213 (Brown, et al. (1990) *J Immunology* 144, 2184–2189, which is incorporated herein by reference) which inhibits GM-CSF binding to HL-60 cells and neutralizes GM-CSF induced colony formation. Screening with radioiodinated 126.213 yielded several binding clones, including one that inhibited immunoprecipitation of GM-CSF by 126.213. Comparison of the recombinant $V_L$ sequence with the human GM-CSF sequence revealed similarity most market in the CDR III region with amino acids 71–78 of human GM-CSF. A synthetic peptide containing this epitope was bound by the neutralizing anti-GM-CSF mAb. Both the recombinant $V_L$ and the peptide containing amino acids 71–78 inhibited the growth of GM-CSF dependent cells. These studies indicate the feasibility of using recombinant antibody libraries as sources of interaction site analogs.

MATERIALS AND METHODS

Bacterial Strains: *E. Coli* DH5 alpha competent cells (BRL, Gaithersburg, Md.) were used for transformation. Bacteria were grown in Luria broth containing 100 mg/ml ampicillin (LB/amp). Solid media contained 1.5% agar (Difco inc.).

Enzymes and oligonucleotides: Restriction endonucleases and T4 DNA ligase were purchased from BRL. Enzyme reaction conditions were according to that of the supplier. Oligonucleotides for PCR primers and for Southern blotting were synthesized by the DNA Synthesis Facility of the Wistar Institute. The primers were selected by analysis of immunoglobulin sequences as published by Kabat (Kabat, et al. (1991) (Bethesda, Md.) 2597, which is incorporated herein by reference). The specific primers are listed in Table 1. PCR amplification employed primers 3315 (relatively specific for the murine $V_\kappa$ III family) and 5591 (near the 3' end of the $C_\kappa$ coding region). Note that primer 5591 introduces a stop codon at codon 207, resulting in a truncated light chain lacking the carboxy terminal 8 amino acids including the cysteine at position 214. This should result in production of light chains which are predicted to remain monomers. Primers were tested on various hybridoma cell lines in the laboratory prior to their use in library construction. In these studies amplified sequences were isolated from the gels cloned and sequenced to verify the utility of the primers and their specificity for amplification of Ig variable regions.

Plasmid construction: The DNA coding for the pectate lyase (pelB) signal peptide of *Erwinia carotovora* was synthesized according to the published sequence (Lei, et al. (1987) *J Bacteriol* 169, 4379–4383, which is incorporated herein by reference) and made double-stranded by PCR. Appropriate restriction sites were incorporated into the primers for insertion into pUC19. Positive transformants were selected and plasmid preps were made. The pelB insert was excised by the appropriate endonucleases and identified by agarose gel electrophoresis. The resultant plasmid (pDAB$_L$) is of utility for protein expression. In these studies we demonstrated that this vector could direct expression of mammalian proteins to both the periplasmic space as well as the bacterial membrane. The proteins expressed in this system were also similar in their conformational characteristics to proteins expressed in mammalian expression systems rather than inaccurately folded and processed in the bacterial cytoplasmic compartment.

Cell Lines and Proliferation Assay: AML 193 cells were obtained from the American Type Culture Collection (ATCC), and MO7E cells were from R. Zollner, Genetics Institute, (Cambridge Mass.). AML 193 was grown serum free in Iscove's modified Dulbecco's media (IMDM) with insulin (10 µg/ml), transferrin (5–10 U/ml), 1% OPI media additive (oxalate, pyruvate and insulin), and GM-CSF 0.5 ng/ml. MO7E was grown in Dulbecco's modified Eagle's media (DMEM) with 10% heat inactivated FCS, Pen/strep, L-glutamine, and GM-CSF 0.5 ng/ml. For proliferation assays, $2 \times 10^4$ AML 193 or MO7E cells were cultured per well in 96 well round bottomed plates in the above media along with test antisera in a final volume of 200 µl. Following a 3–5 day incubation, tritiated thymidine (1 µCi/well) was added for an additional 18 hours, the cells harvested onto glass fiber filters utilizing a PhD cell harvester, and CPM incorporated determined in a standard liquid scintillation system.

Development of Anti-GM-CSF and Anti-anti-GM-CSF: Recombinant human GM-CSF (obtained from Bachem Biosciences, Philadelphia, Pa.) was used to immunize Balb/c mice. Serum was obtained one week following each boost with antigen. Antisera from 3–5 animals was pooled for the assays performed. Following the third boost, significant neutralizing titers against human GM-CSF dependent cellular proliferation were demonstrated. The mice were bled after five boosts, and IgG purified from serum by affinity chromatography with sepharose-protein A. This was used to immunize synergeneic Balb/c mice (50 µg purified IgG per immunization), and serum obtained following each boost. The sera were assayed for inhibition of GM-CSF dependent proliferation, and significant (>50%) inhibition was seen following the eighth boost against both MO07E and AML193 cells. Mice that exhibited neutralizing activity on this assay served as spleen cell donors.

Figure 2:
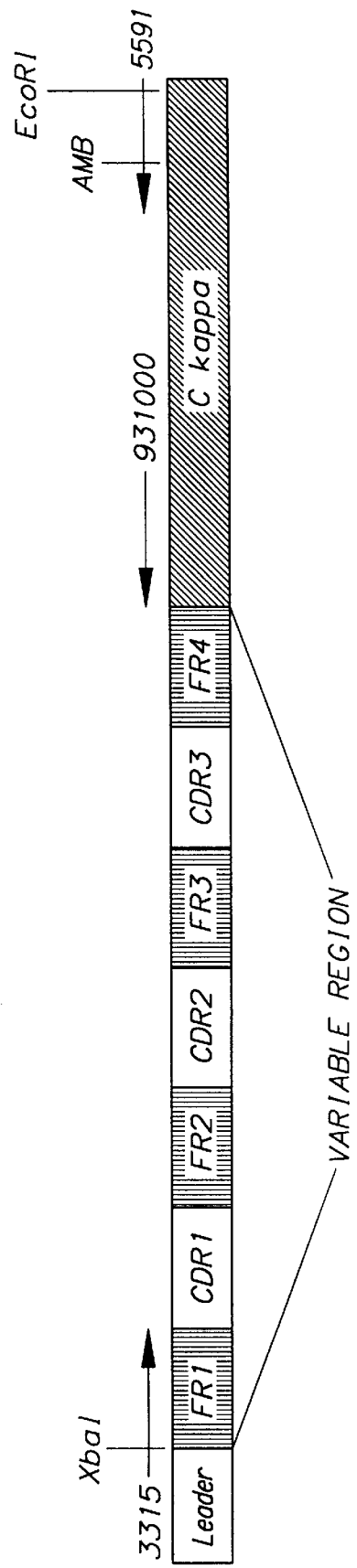
Figure 3A:
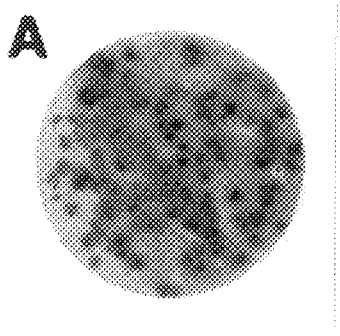
Figure 3B:
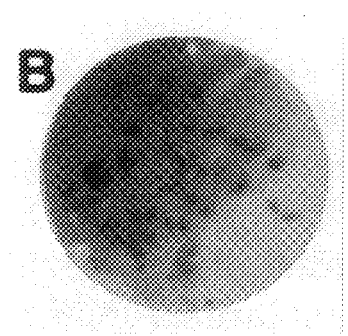
Figure 3C:
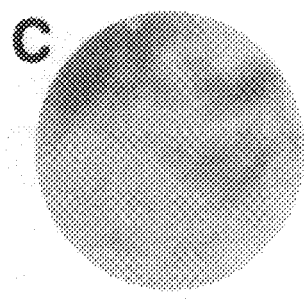
Figure 3D:
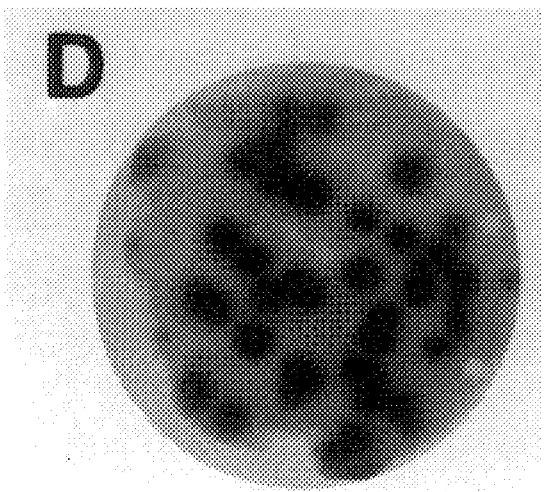
Figure 3E:
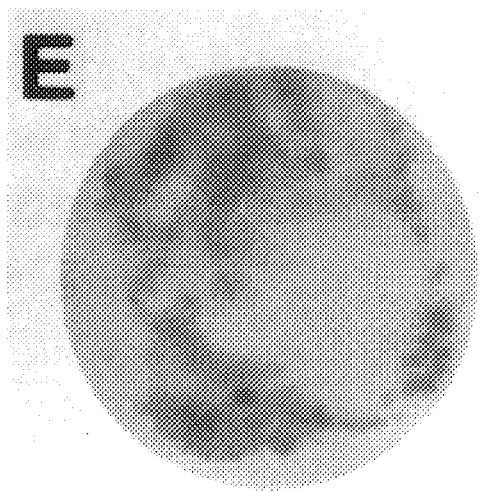

Amplification of Anti-Anti-GM-CSF Immunoglobulin Light Chain Variable Regions ($V_L$) Spleenocytes were isolated from 4 anti-GM-CSF immunized mice who displayed neutralizing activity against GM-CSF dependent proliferation. A cell suspension was prepared, and red blood cells lysed with Gey's solution. Cells were resuspended in guanidinium isothiocyanate (GITC) solution, and vortexed for 30 seconds. 0.1 ml 2 M sodium acetate pH 4 was added, the solution vortexed, followed by 1.0 ml diethylpyrocarbonate (DEP)-water-saturated phenol, the sample mixed, then 0.2 ml phenol/chloroform/isoamyl alcohol, thorough vortexing, and the solution transferred to sterile eppendorf tubes. This was then incubated on ice for 20 minutes, microfuged for 10 minutes, and the top layer recovered, RNA precipitated with 2.5 volumes of 100% ethanol and 1/10 volume 1M sodium acetate pH 5.5 in dry ice/ethanol for 30 minutes. The solutions were microfuged for 15 minutes, the supernatant decanted, the pellets washed in 70% ethanol and rotary evaporated. The dried pellets were resuspended in 50 µl DEP-water and RNA quantified spectrophotometrically. For reverse transcription, 1–20 µg of RNA in 10 µl was utilized to synthesize cDNA primed with random hexamers in the following reaction mixture: 3 µl Maloney Murine Leukemia Virus reverse transcriptase with 6 µl 5 X reverse transcriptase buffer, 1.5 µl RNAse inhibitor, and 3 µl 0.1 M dithiothreitol (all from GIBCO/BRL, Gaithersburg, Md.), 3 µl (100 pmoles) random hexamers (from Pharmacia LKB Biotechnology, Piscataway, N.J.), and either 1 or 3 µl 100 mM dNTPs (25 mM in each dNTP, from Boehringer Mannheim, GmbH W. Germany). Following a 10 minute preincubation at 25° C., the reaction was carried out for 1 hour at 42° C., then 95° C. for 5 minutes followed by storage at −20° C. until use. For PCR amplification, the oligonucleotide primers 3315 and 5591 listed in Table 1 were employed at 0.2 µg/ml final concentrations. The relative position of these primers on Ig$_\kappa$ cDNA is shown in FIG. 2. The PCR cocktail (100 µl) consisted of 16 µl dNTPs (final concentration 200 µM in each dNTP), 10 µl PCR buffer (10x; Perkin-Elmer Cetus Corp., Norwalk, Conn.), 58.5 µl dH$_2$O, 5 µl cDNA and 1.2 units taq polymerase (Perkin-Elmer Cetus Corp.). Amplification was carried out in a Programmable Thermal Cycler (MJ Research, Watertown, Md.). The amplification program was 94° C. for 60 seconds; 52° C. for 90 seconds; and 72° C. for 120 seconds. Following 30 cycles, the temperature was held at 72° C. for 5 minutes. Positive amplification was determined by agarose gel electrophoresis. The PCR products and plasmid DNA were cut with the appropriate endonucleases and plasmid DNA was treated with calf intestinal phosphatase (Boehringer Mannheim; Indianapolis, Ind.), followed by ligation using 1 U of T4 DNA ligase overnight at 16° C. Ligation mixtures were transformed into E. coli DH5a competent cells as described by the manufacturer.

Southern hybridization: Competent E. coli transformed with the amplified $V_\kappa$/pDAB$_L$ library was plated on LB/amp plates. The 5' and 3' PCR primers and an internal oligonucleotide probe for the FR4 region (Table 1) were used for colony hybridization. The probes (100 ng) were labeled with $^{32}$p for 34 minutes using T4 polynucleotide kinase. Nitrocellulose filters (0.45 um; Schleicher & Schuell, Keene, N.H.) were used to lift the transformed bacteria. Following alkaline lysis of the bacteria, the filters were incubated with the labeled probe for 2 hours at 55° C. The filters were then washed two times at room temperature with 2x SSPE and 0.1% SDS. The nitrocellulose filters were exposed to X-ray for 6–48 hours. This revealed inserts present in >65% of the colonies present. This was confirmed by plasmid miniprep analysis.

Protein expression; Bacterial clones possessing the V$\kappa$ genes inserted into pDAB$_L$ were plated onto LB/amp plates. Control plates contained E. coli transformed with either pDAB$_L$ alone, pUC19 or pUC18. Following overnight growth, replica plating, and additional overnight growth, 0.45 μm nitrocellulose filters were placed on the bacterial plate. Filters were lifted to other LB/AMP plates on which 100 μl of isopropyl-β-thio-galactopyranoside (IPTG) (25 mg/ml; Stratagene, La Jolla, Calif.) had been spread and were then incubated for 4 hours at 37° C. Filters were then exposed to chloroform vapor for 15 minutes and incubated overnight (with shaking) in lysis buffer (100 mM Tris-Cl, pH 7.8; 150 mM NaCl; 5 mM MgCl$_2$; 1.5% bovine serum albumin (BSA); 1 μg/ml pancreatic DNAse I; and 40 μg/ml lysozyme). Filters were then blocked for 4 hours with blocking buffer (4% non-fat dry milk and 1% BSA in Tris-buffered saline (TBS; 20 mM Tris, 500 mM NaCl; pH7.5)). Following blocking, filters were screened for specific variable region expression as noted below, or evaluated for protein expression by binding of polyvalent anti-murine antibodies. For this, blocked filters were incubated with peroxidase- conjugated goat anti-mouse polyvalent antisera (Sigma Chemical Co., St. Louis, Mo.) diluted 1:1,000 in blocking buffer. Following a 1 hour incubation; filters were washed three times with TBS 0.05% Tween 20 (10 minutes per wash), then with TBS alone once. For development, filters were incubated in 5 ml TM Blue™ Precipitating Reagent, (Transgenic Sciences, Worcester, Ma.) for 2–5 minutes at room temperature until color development was apparent. The filters were washed with dH$_2$O, and dried. This confirmed expression of immunoglobulin fragments in ~60% of the colonies. For some experiments, lysates were prepared of bacteria expressing the recombinant antibody fragments. Lysates of E. coli XL1 Blue cells (Stratagene, LaJolla, Calif.) were prepared either from unmanipulated bacteria or E. coli transformed with pDAB$_L$ alone, or the various V$_L$ regions ligated into pDAB$_L$. Colonies were grown overnight in LB/Amp, and 500 μl used to seed 5 ml cultures grown to ~0.6 OD 450 units in Superbroth (Cell Center, University of Pa.), then induced with 1 mM isopropylthiogalactoside (IPTG) for 4–12 hours. The cells were centrifuged (10,000 RPM for 30 minutes), and the pellets dissolved in 2 mls of lysis buffer (10 mM Tris-HCl pH 8.0, 100 mM NaCl, 0.5 mM EDTA, 1 mM phenylmethylsulfonyl fluoride, and aprotinin diluted 1:100 from a concentration of 2.1 mg/ml, all from Sigma) . These cells were sonicated for 45 seconds on ice and clarified by centrifugation (11,000 for 15 minutes at 4° C.) and the supernatant (lysate) used as sources of V$_L$ fragments.

Library Screening: For binding of $^{125}$I-labelled 126.213, blocked filters were incubated for 2 hours at room temperature with $^{125}$I-labelled 126.213 (purified by staphylococcal protein A affinity chromatography), 500,000–1,000,000 CPM/ml, labelled by the chloramine T method in TBS containing 1% BSA and 0.1% Tween-20 (TBS/BSA). Filters were washed extensively with TBS/BSA and autoradiographed (Kodak XRP film) for 2–24 hours.

Western Blotting: Bacterial lysates (prepared as above) or recombinant human GM-CSF were run on 15% SDS-polyacrylamide gel in reducing sample buffer (2% SDS 50 mM Tris HCl pH 6.8, 10% glycerol, 0.001% bromophenol blue) with 500 μg bacterial protein (as determined by the Bio-Rad protein assay) loaded in each well. Following electrophoresis, the gel was transferred to Immobilon P transfer membranes (Millipore) as described, and the blot blocked with 1% bovine serum albumin, 5% non-fat dry milk, 0.005% Tween 20 in phosphate buffered saline (blocking buffer) for >1 hour at 37° C. or overnight at 4° C. The blots were then incubated with 5 mls purified mAb 126.213 diluted to 2 μg/ml in blocking buffer for 2 hours at 37° C., and washed 4 x in PBS 0.05% Tween 20 (wash buffer). Radioiodinated polyclonal goat anti-mouse IgG (Sigma) was then added (1,000 CPM/μl in blocking buffer) and the blot incubated for 2 hours at 37° C., washed extensively in wash buffer, dried and exposed for 12=72 hours to Kodak XAR film.

Immunoprecipitation: 5 μg purified 126.213 was reacted with protein G beads (Sigma, St. Louis, Mo.) in eppendorf tubes and rotated overnight at 4° C. The tubes were centrifuged and the liquid aspirated. The beads were then washed 3X with lysis buffer (1% Triton, 0.05% SDS, 10 mM Na$_2$HPO$_4$—NaH$_2$PO$_4$, 150 mM NaCl, 5 mM EDTA, 100 μM Na$_3$PO$_4$ and 5 μg/ml Aprotinin all from Sigma) to remove unbound antibody. The beads were resuspended in 100 μl lysis buffer and $^{125}$1I-GM-CSF was added to the tubes in the presence or absence of inhibitors (100 μl total volume) and rotated at 4° C. for one hour. The tubes were then centrifuged, the liquid discarded and the beads washed 3X. The beads were then resuspended in 2X sample buffer (0.5 M Tris HCl pH 6.8. 16% Glycerol, 3.2% SDS, 8% 2-ME and 0.04% Bromphenol Blue (all from Sigma) in distilled H$_2$O) and heated at 95° C. for 5 minutes to dissociate bonds. Samples were then loaded onto 10% SDS PAGE gels and analyzed by autoradiography.

Radioreceptor Binding Assay: This was modified from previously published protocols. Briefly, HL-60 cells (from ATCC) were grown in RPMI 1640 with 10% FCS and added L-glutamine. 2x10$^6$ HL-60 cells were washed twice in RPMI 1640 with 1% BSA and 25 mM Hepes pH 7.4 (binding buffer), centrifuged and incubated with inhibitors as noted in figure legends in a 100 μl volume for 1 hour at room temperature. 10 μl of $^{125}$I-GM-CSF (~500,000 CPM) was then added for 30 minutes at room temperature, the cells layered over 500 μl chilled FCS, centrifuged, and the pellets counted.

Peptide Synthesis: All peptides were synthesized by solid-phase methods as previously described (Williams, et al., (1988) Proc Natl Acad Sci USA 85, 6488–6492; Williams, et al. (1989) Proc Natl Acad Sci USA 86, 5537–5541; Williams, et al., (1991) J Biol Chem 266, 9241–9250; and Williams, et al. (1991) J. Biol Chem 266, 5182–5190) by the Wistar Institute peptide synthesis facility or Macromolecular Resources at Colorado State University, deprotected and released from the resin using anhydrous HF.

Enzyme Linked Immunosorbent Assay (ELISA): ELISA was performed with polystyrene plates (Dynatech Laboratories Inc.) coated with peptide by evaporation of peptides (at the concentrations noted) in distilled water overnight at 37° C. The wells were washed with PBS, blocked with 0.05% Tween, 2% bovine serum albumin (BSA) in PBS and washed with PBS. Primary antibodies were added at varying dilutions for >1 hour at 37° C. After washing, secondary antibody, goat anti-mouse conjugated to horse radish peroxidase (HRP; Sigma Chemical Co., St. Louis, Mo.) was added per well in 1% BSA in PBS for 1–2 hours at 37° C., the substrate used for color development 3,3', 5,5' tetramethyl-benzidine dihydrochloride (TMB, Sigma Chemical Co.). The wells were decanted, washed extensively, and absorbance of samples was measured in a plate reader (MR 5000; Dynatech Laboratories) and expressed as OD 450 nm. Specific values were determined by subtracting the absorbance measured from uncoated wells from the absorbance to peptide coated wells.

RESULTS

Construction and Screening of Anti-Anti-GM-CSF $V_LC_\kappa$ Library: Polyclonal neutralizing antibodies against human GM-CSf raised in Balb/c mice were used to develop syngeneic anti-anti-GM-CSF with neutralizing activity (FIG. 1). The polymerase chain reaction (PCR) was used to amplify immunoglobulin Vκ genes from these mice. Oligonucleotide primers for amplification of immunoglobulin genes were chosen based on conserved DNA sequences found in $V_L$ variable framework regions and from the kappa constant region domain. The 5' primer used in these experiments was relatively specific for the VκIII family. The 3' primer introduced a stop codon at position 207, eliminating 8 amino acids including the carboxy terminal cysteine residue, thereby eliminating the tendency for the produced light chains to dimerize. Spleen cells were isolated, RNA extracted, and cDNA synthesized. This served as a template for PCR amplification of the $V_LC_\kappa$ regions. Bands of the expected size (~680 bp) were observed following agarose gel electrophoresis. This amplification was specific as control cellular DNA from human T lymphocyte cell lines did not yield a PCR product.

The PCR products were ethanol precipitated (to remove residual primer DNA) and digested with appropriate restriction endonucleases (XbaI and EcoR1). These were ligated into similarly restricted, alkaline phosphatase treated PDABL. Following ligation, the reaction products were transformed into E. coli DH5α cells and plated onto 30 LB/amp plates. This $V_LC_\kappa$ library was then screened after induction with IPTG with radioiodinated neutralizing mAb 126.213, which specifically neutralizes GM-CSF activity. Thirty filters containing 500–1,000 colonies each were screened in this manner. Representative filters are shown in FIG. 3. Based on the observed binding of $^{125}$I-126.213 to colonies, we picked 30 reactive colonies. These were expanded and replated and rescreened using fresh $^{125}$I-126.213 and a control mAb (ID6) specific for HIV-1 gp120 (38). Approximately 50% of the filters were bound by $^{125}$I-126.213 but not by $^{125}$I-ID6 following the second round of screening (FIG. 3). Most of these were bound by $^{125}$I-126.213 in subsequent rounds of screening. Ten colonies which were consistently bound by $^{125}$I-126.213 but not $^{125}$I -ID6 in subsequent assays were selected for further characterization.

Figures 4A, 4B:
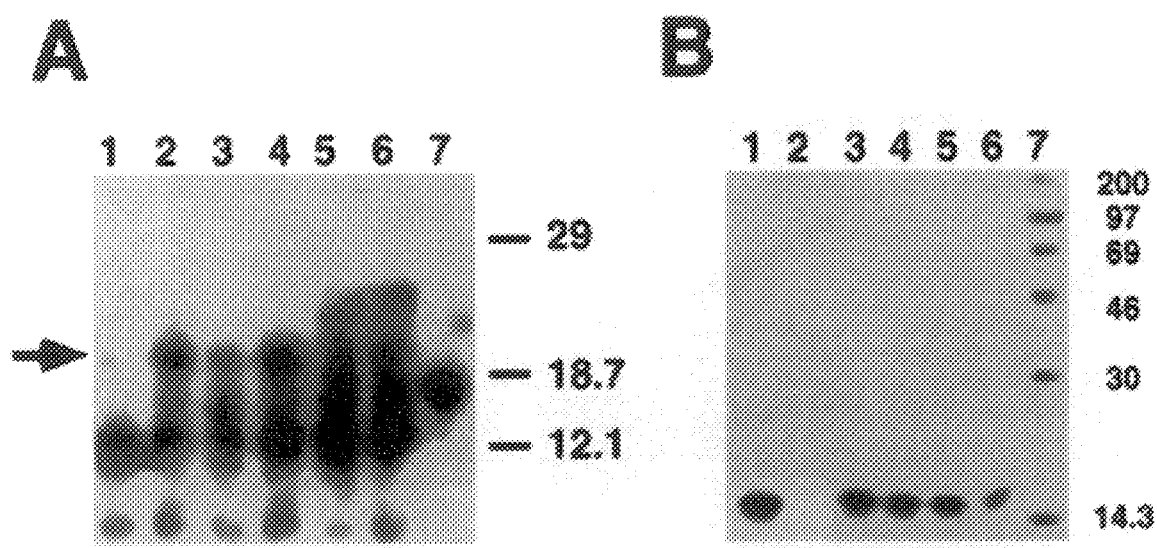
Figure 4C:
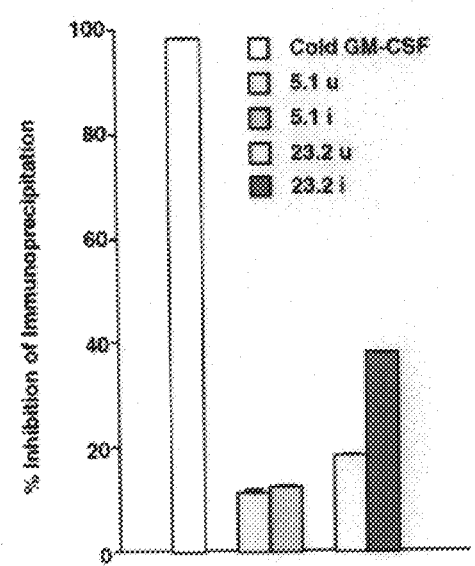
Figure 4D:
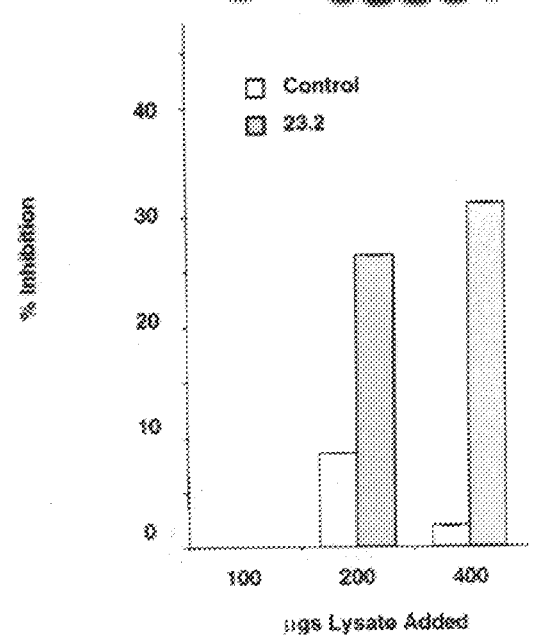
Figure 5:
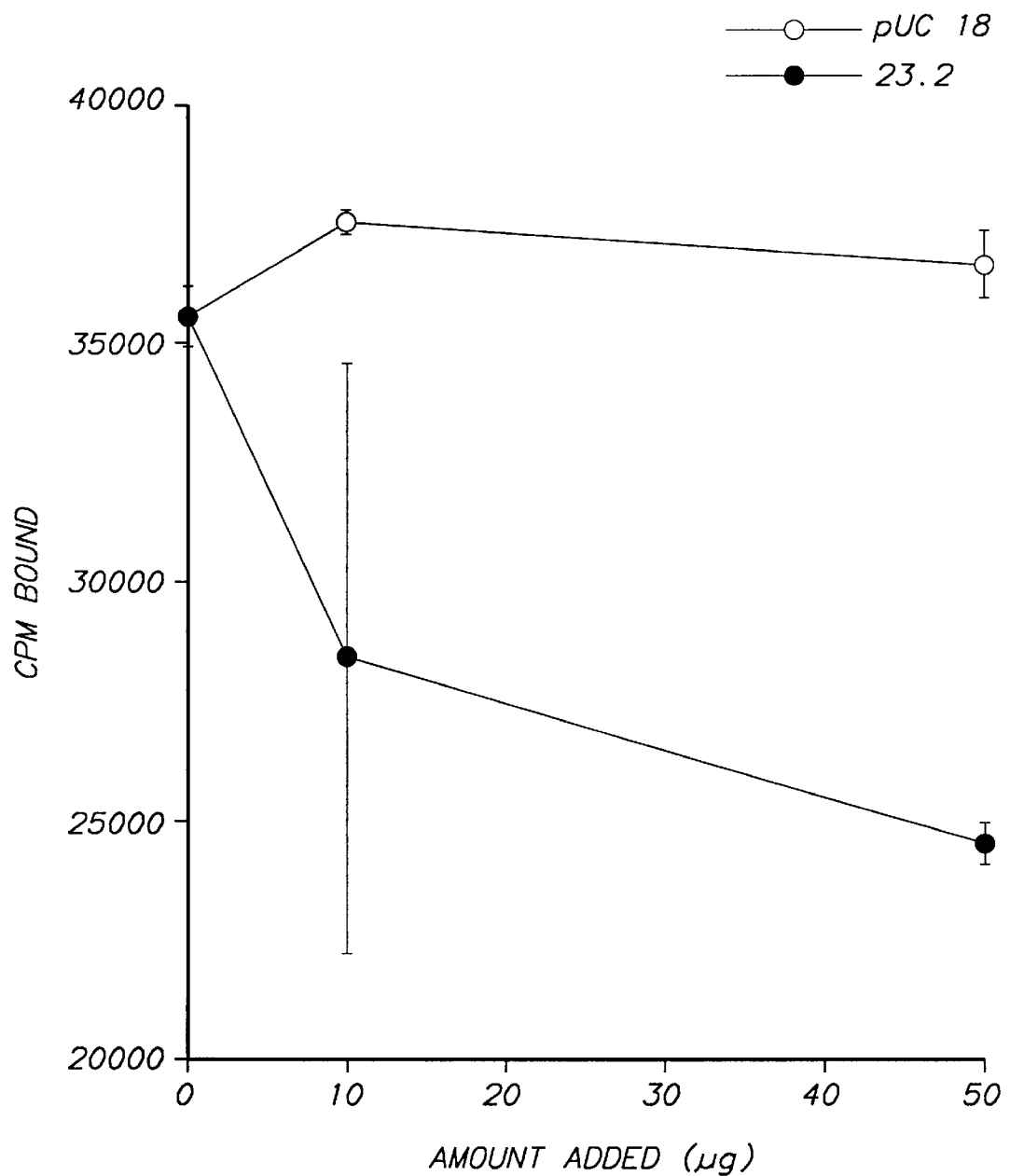
Figure 6A:
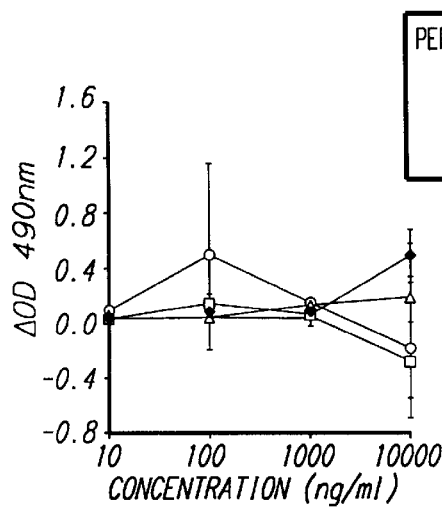
Figure 6B:
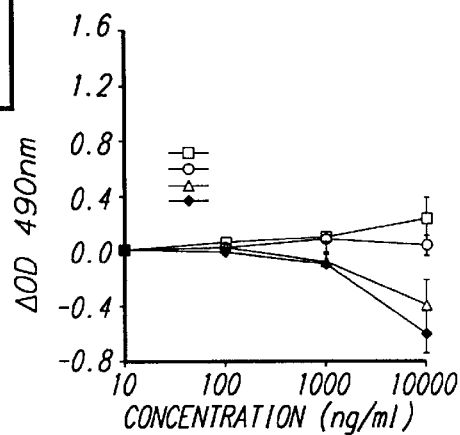
Figure 6C:
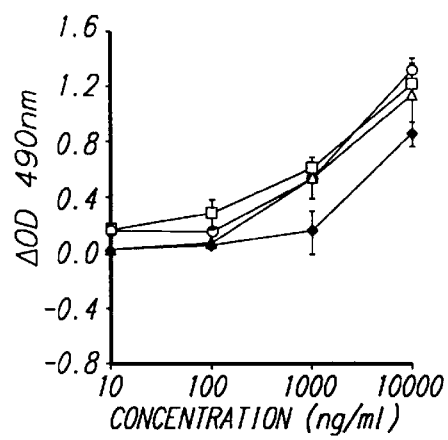
Figure 6D:
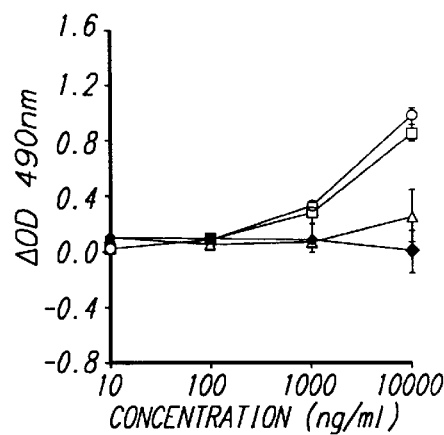
Figure 6E:
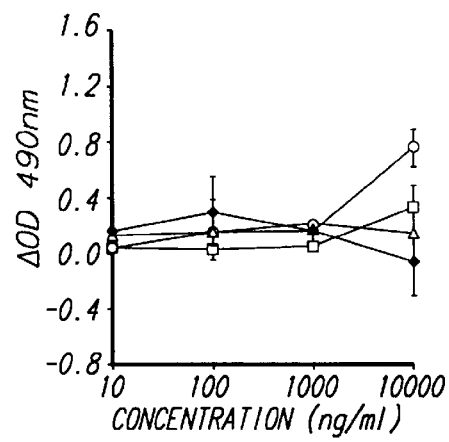
Figure 6F:
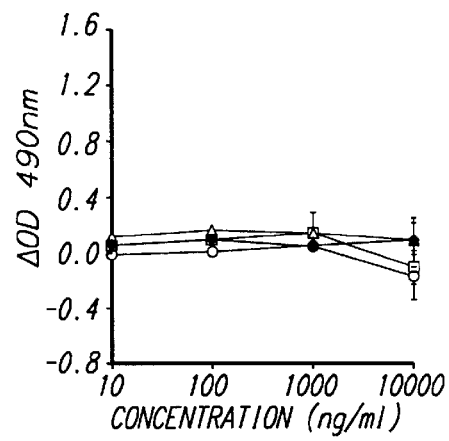

Characterization of $V_LC_\kappa$ Regions: Western blot analysis was performed of bacterial lysates prepared from the bacterial colonies consistently bound by 126.213. For Western analysis, lysates were prepared from E. coli transformed with the PDABL plasmid alone, or containing the specific $V_L$ region inserts. The cultures were then either left uninduced or induced with IPTG, bacterial lysates prepared, separated electrophoretically and transferred to Immobilon filters. These were probed with 126.213 followed by $^{125}$I-goat anti-mouse IgG and analyzed by autoradiography. A typical Western blot is shown in FIG. 4. This compares cultures of bacteria both uninduced and following induction with IPTG. As can be seen, IPTG induces the appearance of a ~21–23 kd MW band for the clones containing specific $V_L$ regions, while only non-specific bands are present in the cultures transformed with pDAB$_L$ regions, while only non-specific bands are present in the cultures transformed with PDABL alone. Notably, this gel was run under non-reducing conditions, suggesting that the $V_L$ fragments do not dimerize, instead remaining as monomers. The molecular weight of the band detected is somewhat lower than the 23 kd predicted for the isolated VL region. This may be due to inaccuracy of the molecular weight markers used, or could reflect compact folding of the $V_LC_\kappa$ fragments.

The neutralizing mAb 126.213 specifically immunoprecipitates $^{125}$I-GM-CSF. This assay allowed investigation of the ability of various rAb $V_LC_\kappa$ regions to compete with $^{125}$I-GM-CSF binding to 126.213. Of the 10 rAb $V_LC_\kappa$ regions screened, only one (clone 23.2) reproducibly inhibited immunoprecipitation by 126.213 (FIG. 4). Inhibition with the lysates from bacteria transformed with 23.2 reproducibly inhibited immunoprecipitation by up to 40 %. Inhibition was much greater for IPTG induced cell lysates compared with uninduced lysates (FIG. 4). Clone 23.2 was selected for further characterization.

Inhibition of GM-CSF Binding to HL-60 Cells by 23.2. GM-CSF specifically binds GM-CSF receptors present on HL60 (human myelomonocytic leukemia) cells, and this binding is inhibited by 126.213. We examined the ability of rAb 23.2 to inhibit binding of $^{125}$I-GM-CSF to HL60 cells on a standard cellular binding assay. In this assay, HL-60 cells were preincubated with lysates from E. coli induced with IPTG following transformation with the 23.2 plasmid or an irrelevant plasmid (pUC18). 23.2 transformed bacterial lysates inhibited binding of $^{125}$I-GM-CSF to HL-60 cells, while control lysates had no effect. This result indicates that 23.2 competes with GM- CSF for binding to a site on HL-60 cells, and may bind to the CM-CSF receptor present on these cells.

Sequence of Clone 23.2: As clone 23.2 was specifically bound by mAb 126.213, and competed with GM-CSF for binding to 126.213 and to HL-60 cells, the 23.2 insert was sequenced. The nucleic acid sequence and derived amino acid sequence of 23.2 was determined. The 23.2 $V_L$ region is a member of the murine VKIII family as defined by Kabat, or the Vκ21 group as defined by Weigert (Weigert, et al. (1978) Nature 276, 785–790, which is incorporated herein by reference), with the J region derived from the Jκ1 family. Database searching reveals that the 23.2 V/J amino acid sequence is very similar to the previously described Vκ21 hybridoma light chains 6684 and 7940 derived from NZB mice, differing by only 6 amino acid substitutions from 6684 and 8 substitutions from 7940.

The sequence of 23.2 was compared with the human GM-CSF sequence using the Bestfit, Gap, Wordsearch and Segments programs of the Wisconsin package. Several regions of sequence similarity were noted which involved CDR regions of 23.2. Interestingly, all of the CDR regions displayed sequence similarity to amino acids 70–104 of GM-CSF. Prior studies of 126.213 used murine/human chimeric forms of GM-CSF to map intersection sites. These studies indicated binding to chimerics containing amino acids 18–111 and 18–100 derived from the human sequence, but lack of binding to a chimeric which derived amino acids 18–94 from the human sequence and all others from the murine sequence. This suggested that residues 94–100 were critical for 126.213 binding to GM-CSF. A region of high sequence similarity is seen between amino acids 71–78 of GM-CSF and the CDR III of 23.2. This region shows 5 identical amino acids when gaps are introduced between the sequences to allow alignment of the relevant residues. Interestingly, amino acids 71–78 (on the B helix of GM-CSF) lie immediately adjacent to amino acids 94–100 (on the C helix) in the crystal structure of GM-CSF. Based on this analysis, we reevaluated 126.213 epitope recognition utilizing synthetic peptides.

Mapping of 126.213 with Synthetic Peptides: Synthetic peptides were available corresponding to amino acids 18–34 (pep4), 34–48 (p29), 48–71 (pep5), 71–95 (pep3), 95–115 (p28) and 113–129 (pep6) of the human GM-CSF molecule. (Note that amino acids 1–18 correspond to the leader peptide, and residues 130–144 can be deleted without affecting GM-CSF binding or bioactivity). These peptides were used in ELISA assays to assess binding of 126.213 and a control isotype matched monoclonal antibody. As shown in FIG. 6, 126.213 demonstrates significant binding (>3 SDs of control BSA coated plate) at several concentrations to pep5 and pep3. These peptides represent a continuous epitope from residue 48 through residue 95 of GM-CSF. No significant binding was seen to the other peptides evaluated, nor did a control isotype matched mAb bind to any of the peptides in this assay. Thus, while studies of chimeric human/murine GM-CSF molecules implicates residues 94–100 in 126.213 binding, the peptide mapping studies in FIG. 6 suggest that residues 48–95 may also be involved. This includes residues 71–78, which share sequence similarity with the 23.2 CDR I region. This led us to explore the activity of the peptides described in radioreceptor assays.

Figure 7:
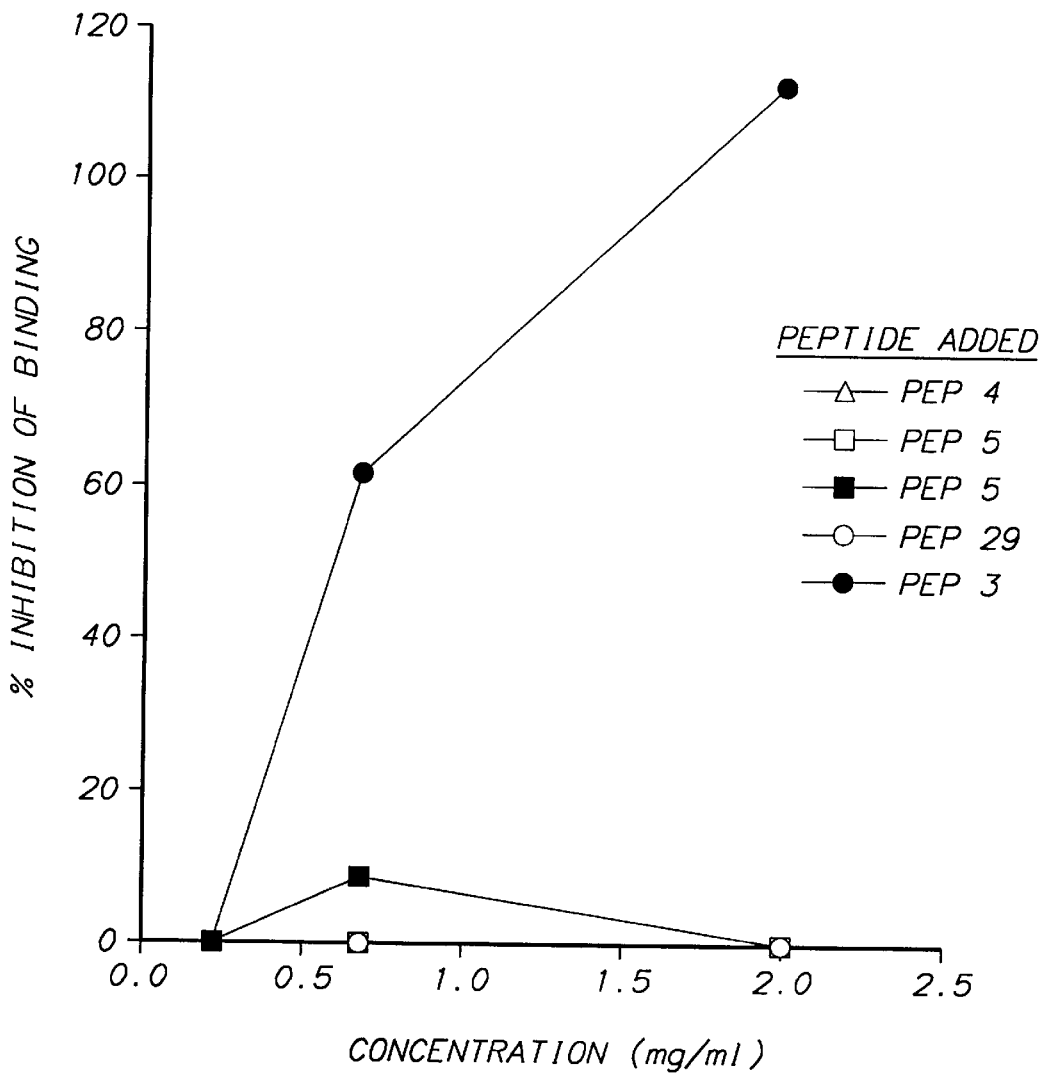

Inhibition of GM-CSF Binding to HL-60 Cells by pep3: The radioreceptor assay described above was used to evaluate the ability of the synthetic peptides to inhibit binding of $^{125}$I-GM-CSF to HL-60 cells. The results are shown in FIG. 7. Of the peptides evaluated, only pep3 inhibited binding of $^{125}$I-GM-CSF to HL-60 cells. None of the other peptides evaluated had any activity in this assay. p28, while not included in this experiment, did not demonstrate any activity in related assays. These results indicate that pep3 inhibits $^{125}$I-GM-CSF to HL-60 cells, and suggests that pep3 binds to GM-CSF receptors on these cells.

DISCUSSION

GM-CSF activity is mediated by binding to specific cellular receptors (GM-CSFR) which belong to a recently described supergene family. The high affinity GM-CSFR is comprised of an alpha chain (GM-CSFRα) specific for GM-CSF, and a beta chain ($\beta_c$), which can also associate with the interleukin-3 (IL-3) and IL-5 receptor alpha chains. The GM-CSFRα is felt to impart specificity to the interaction with GM-CSF, and when expressed without c is able to bind GM-CSF, albeit with lower affinity than the heterodimeric receptor.

GM-CSFRA is organized into a large (298 residue) external domain, a single transmembrane segment, and a short (54 residues) cytoplasmic tail. GM-CSFRα has been included into a new receptor supergene family which includes the interleukin-2 receptor β subunit, interleukin-4 receptor, interleukin-6 receptor, interleukin-7 receptor, erythropoietin receptor, prolactin receptor, and growth hormone receptor. The members of this receptor supergene family all appear to contain a domain with sequence homology to the type III modules of fibronectin. This is of interest, as the tenth type III domain of fibronectin contains the RGD sequence which interacts with the fibronectin receptor. The corresponding region of the GM-CSFRA family contains the WSxWSE box, which is a characteristic motif of these receptors, and some have suggested a similar role for this region in ligand interaction. $\beta_c$ does not appear to bind IL-3 or GM-CSF directly. However, co-expression with the GM-CSFRα protein reconstitutes high affinity binding for GM-CSF. $\beta_c$ is organized into a 423 residue external domain, a single transmembrane domain, and a 432 residue cytoplasmic domain. Signal transduction following binding to GM-CSF receptors has been studies by introducing the GM-CSFRα and $\beta_c$ genes into NIH3T3 and BA/F3 cells, and the reconstituted high affinity receptor, but not GM-CSFRα alone, transduces signals including tyrosine kinase activity, phosphorylation of Raf-1, the induction of c-fos and c-myc mRNAs, and induction of a transformed phenotype in the presence of GM-CSF. Both GM-CSF and IL-3 have been reported to induce tyrosine kinase activity and phosphorylation of the c-fps/fes proto-oncogene produce (p92c-fes) in human erythroleukemia cells, and GM-CSF induces the association of $\beta_c$ with p92c-fes. However, other studies indicate that binding of GM-CSF to the low affinity receptor (GM-CSFRa) alone is sufficient to mediate signal transduction in other cells.

GM-CSF binding and bioactivity has been analyzed at a molecular level both biochemically and molecularly utilizing mutagenesis protocols. Two disulfide bridges have been demonstrated by biochemical methods between cysteines at positions 51–93, and 85–118, with one of these (51–93) felt to be critical for biological activity. In vitro mutagenesis and expression of mutants in COS cells revealed that residues in regions 11–15, 24–37, 47–49, and 81–89 are critical for activity. Scanning-deletion analysis of murine GM-CSF indicated four regions critical for biological activity, spanning amino acids 18–22, 34–41, 52–61, and 94–115. One problem with deletion mutagenesis is the proclivity to induce alterations in molecular structure at sites distant from the mutation. More subtle alterations in molecular structure are needed to map out regions critical for biological activity that do not affect the overall shape of the molecule. This has been aided by the observation that murine GM-CSF is ineffective in stimulating human GM-CSFR bearing cells, while human GM-CSF is similarly incapable of affecting murine GM-CSFR bearing cells. Comparative analysis of human versus murine GM-CSF indicates several regions of primary sequence divergence, with overall conservation of 78/144 residues, an additional 16 conservative substitutions, and a 3 amino acid deletion. As the substitutions are scattered throughout the molecule, it was possible to swap regions of murine and human GM-CSF to locate sites critical for receptor interaction. These studies indicated a critical role for amino acids 21–31 and 77–94 in mediating the activity of human GM-CSF. Substitution mutagenesis studies of murine GM-CSF used proline substitutions within the predicted α-helices. Five mutants were identified (E21P, L56P, E60P, L63P, and L107P) which had marked reductions in activity along with hyperglycosylation. (Note that these studies used the mature peptide numbering; deleting the leader peptide subtracts 20 residues from the sequence numbers).

Additional studies have used constructs, antibodies and peptides in an attempt to define regions important for GM-CSF activity. Studies used neutralizing mAbs and murine x human constructs (Brown, et al. (1990) *J Immunology* 144, 2184–2189, which is incorporated herein by reference). This revealed that binding of one mAb to constructs required human residues 18–111, while the other mAb could bind constructs containing human residues 18–100. Neither mAb bound to a construct with human residues 18–96. Mapping of a panel of neutralizing and non-neutralizing mAbs with the murine x human constructs and with synthetic peptides has been performed. The neutralizing mAbs mapped to amino acids 40–77, 78–94, or 110–127. An additional neutralizing mAb was mapped with proteolytic fragments of human GM-CSF, and found to bind a unique immunoreactive hGM-CSF product comprising two peptides, residues 86–93 and 112–127, linked by a disulfide bond between residues 88 and 121. A carboxy terminal peptide derived from residues 110–127 was used in one study which found that this peptide elicited neutralizing antibodies to human GM-CSF. However, this peptide did not appear to directly interact with the receptor. Monoclonal antibodies directed against synthetic peptide analogs of murine GM-CSF derived from the amino terminal region (residues 27–38) also display high neutralizing activity. Studies of synthetic analogs of GM-CSF indicated that peptides containing the core region of amino acids 16–121 retained ≥75% of their activity. Smaller fragments containing amino acids 22–121 or 14–96 retained ≥25% of their activity.

Mutagenesis studies implicate the first (A) helix in binding of GM-CSF to the high affinity alpha/beta GM-CSF receptor, but not to the low affinity receptor (alpha chain alone). This is illustrated most strikingly by studies using mutants of residue Glu21of GM-CSF. These mutants inhibit binding of GM-CSF to the low affinity receptor, but display little activity in inhibiting binding to the high affinity receptor. Based on these experiments, it has been proposed that the first alpha helix of GM-CSF is responsible for binding to the beta chain of the GM-CSF receptor. By analogy, the first alpha helix on IL-5 and IL-3, whose receptors share the common beta chain with GM-CSF, have also been proposed to mediate interaction with the beta chain. However, mutagenesis studies of IL-3 also implicate additional potential sites. Interestingly, on cells that express both GM-CSF and IL-3 receptors, IL-3 competes with GM-CSF for binding to the high affinity receptor, and prevents binding to both receptor subunits (as determined by chemical cross-linking studies) when GM-CSF is present at low (pM) concentrations, while at higher concentrations GM-CSF associates with the GM-CSFRα even in the presence of excess IL-3. These studies also demonstrated that binding of GM-CSF stabilizes the ternary complex of GM-CSF-GM-CSFRα and $β_c$. Solubilized membrane forms of GM-CSFR also form ternary complexes upon ligand binding.

The recent elucidation of the crystal structure of human GM-CSF places these studies in perspective. This reveals a four-helix bundle organization similar in some respects to that described for growth hormone (deVos, et al. (1992) *Science* 255, 306–12, which is incorporated herein by reference), interleukin 2 (Brandhuber, et al. (1987) *Science* 238, 1707–9, which is incorporated herein by reference), and interleukin 4 (Garrett, et al. (1992) *Biochemistry* 31, 4347–53; Powers, et al. (1993) *Biochemistry* 32, 6744–62; Redfield, et al. (1992) *Biochemistry* 31, 10431–7; and Smith, et al. (1992) *J Mol Biol* 224, 899–904; each of which is incorporated herein by reference). The related cytokines macrophage colony stimulating factor (M-CSF) (Pandit, et al. (1992) *Science* 258, 1358–62, which is incorporated herein by reference) and interleukin 5 are organized as dimers of four-helix bundles (Milburn, et al. (1993) *Nature* 363, 172–6, which is incorporated herein by reference). Receptor dimerization appears important for signal transduction in these systems. Engineered IL-5 monomers have no activity in signal transduction, implicating receptor cross-linking as an essential step in signal transduction. The co-crystal structure of human growth hormone with its receptor reveals receptor dimerization mediated by opposing faces of the growth hormone molecule. This suggests that GM-CSF might mediate signal transduction by a similar mechanism.

The studies described here suggest a second binding site on GM-CSF involved in interaction with the GM-CSFRα. This epitope corresponds to regions in the GM-CSF molecule mimicked by the 23.2 rAb fragment. 23.2 was selected to bind to the antigen binding idiotypes of the neutralizing mAb 126.213. 23.2 displays several features characteristic of an "internal image" of the antigen including competition with GM-CSF for binding to 126.213 and to HL-60 cells, and similar amino acid residues implicated in binding. This analysis also led to the observation that a synthetic peptide corresponding to residues 71–95 (pep3) is also capable of competing with GM-CSF binding to HL-60 cells. These observations further implicate these epitopes as interaction sites with the GM-CSFR on HL-60 cells.

In prior studies, we described the molecular basis for antibody mimicry of a viral hemagglutinin (Williams, et al., (1988) *Proc Natl Acad Sci USA* 85, 6488–6492; Williams, et al. (1989) *Proc Natl Acad Sci USA* 86, 5537–5541; Williams, et al., (1991) *J Biol Chem* 266, 9241–9250; and Williams, et al. (1991) *J Biol Chem* 266, 5182–5190). Other groups have applied this technology to platelet fibrinogen receptor (Taub, et al. (1989) *J Biol Chem* 264, 259–265), the thyroid stimulating hormone receptor (Taub, et al. (1992) *J Biol Chem* 267, 5977–84), and epitopes on the hepatitis B surface antigen (Pride, et al. (1992) *Proc Natl Acad Sci USA* 89, 11900–4). These studies in general described mimicry of structures either known or predicted to represent reverse turns. As antibody CDRs are generally reverse turns, the ability of antibody CDRs to mimic other reverse turn regions does not necessarily imply that antibodies can mimic other diverse backbone geometries. The epitope involved in this study is clearly alpha helical in nature. This feature may account for the "spotty" nature of the sequence similarity seen here. In spite of this, computer algorithms were able to pick regions of adequate sequence similarity that correspond to the predicted epitope recognized. This indicates that antibody mimicry of helical regions can be understood on a molecular/structural level. The application of recombinant antibody technology to development of such mimics should broaden the applicability of alternative ligand development in the analysis of active site structures.

Example 2

We have continued our investigations of the recombinant antibody light chain analog of GM-CSF termed 23.2. This recombinant light chain was selected based on its binding to neutralizing mAb 126.213. Based on the sequence of 23.2 and its comparison with GM-CSF, peptides have been synthesized as follows:

| | |
|---|---|
| CDR I Peptide: | Cys Arg Ala Ser Lys Ser Val Ser Ser Ser Gly Tyr Ser Tyr Met His Trp Tyr Gln Gln (SEQ ID NO:1); |
| CDR II Peptide: | Tyr Leu Ala Ser Asn Leu Glu Ser Gly Val Pro Pro Arg Phe Ser Gly Ser (SEQ ID NO:5); |
| CDR III Peptide: | Cys Gln His Ser Arg Glu Leu Pro Trp Thr Phe Gly Gly Gly Thr Arg Leu Glu Ile Lys Arg (SEQ ID NO:2). |

Figure 8:
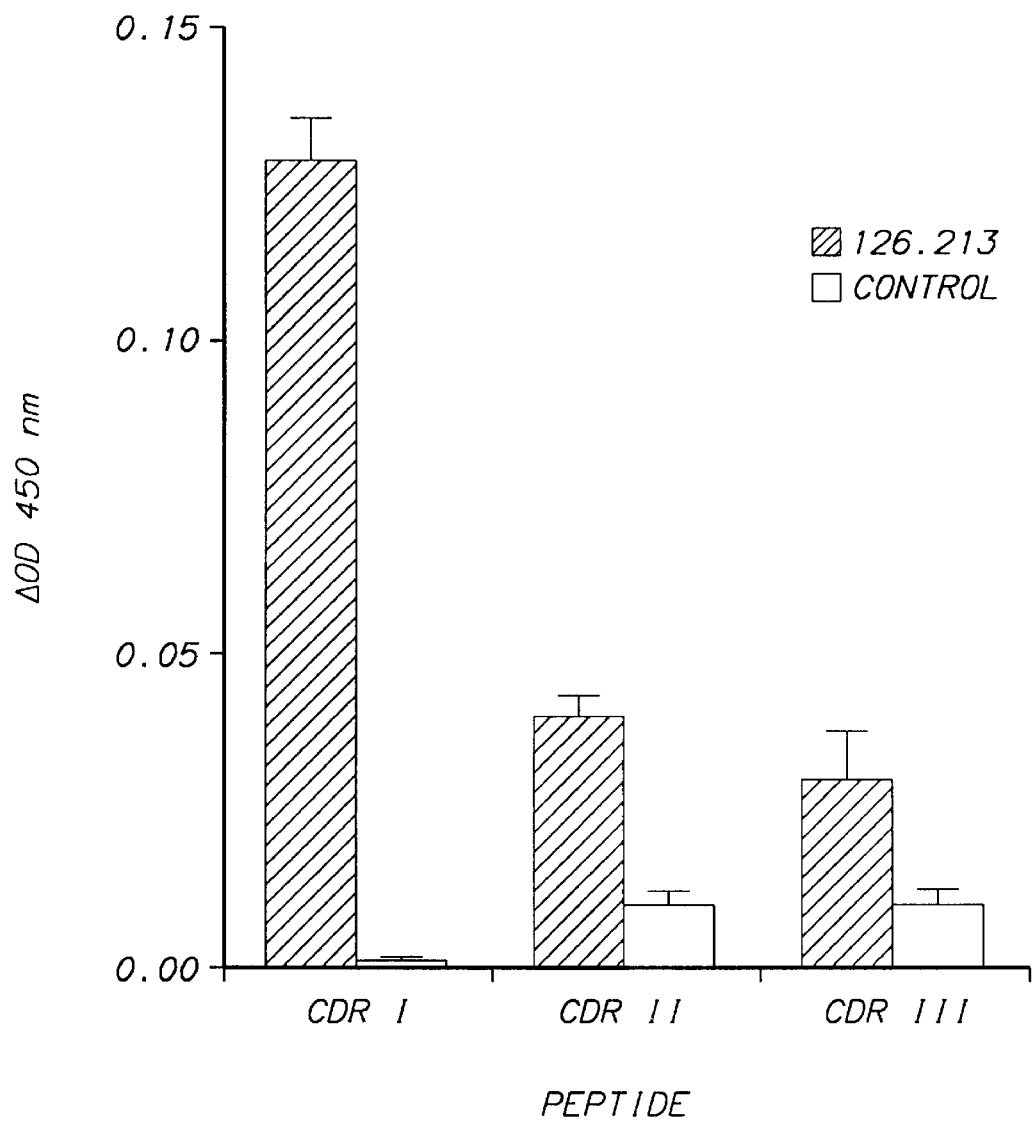
FIG. 8 shows results of binding studies using CDR-derived peptides described in Example 2 and MAb 126.213.

We have performed an initial screening evaluation on ELISA of 126.213 binding to these peptides, in comparison with a control mAb. ELISA wells were coated with peptides by evaporation (1.25 μg/well), blocked and 1 μg/ml purified mAb 126.213 or control isotype matched mAb 9W.A2 incubated on the wells, followed by washing, incubation with HRP-goat-anti-mouse Ig, washing and development of the plate. The result is shown in FIG. 8.

Specific binding of mAb 126.213 to all three peptides is demonstrated. The peptides have also been used in assays to evaluate their bioactivity. The effect of the peptides on the growth of the GM-CSF dependent cell line AML193 was compared with their effects on the growth of the interleukin-2 dependent cell line CTLL. Varying amounts of peptides were added to the cells in a standard proliferation assay. AML 193 cells were obtained from the American Type Culture Collection (ATCC). CTLL cells were performed as described in Borofsky, M.A., et al. (1992) *Immunol. Res* 11:154–164. AML 193 was grown serum free in Iscove's modified Dulbecco's media (IMDM) with insulin (10 μg/ml), transferrin (5–10 U/ml), 1% OPI media additive (oxalate, pyruvate & insulin), and GM-CSF 0.5 ng/ml. For proliferation assays, $2 \times 10^4$ AML 193 cells were cultured per well in 96 well round bottomed plates in the above media along with test peptides in a final volume of 200 μl. Following a 5 day incubation, tritiated thymidine (1 μCi/well) was added for an additional 18 hours, the cells harvested onto glass fiber filters utilizing a PhD cell harvester, and CPM incorporated determined in a standard liquid scintillation system. For the CTLL assay, $5 \times 10^3$ cells were grown per well in RPMI 1640 with 10% FCS, pen/strep, L-glutamine and $5 \times 10^{-5}$ M 2-mercaptoethanol with or without added 10% rat spleen concanavalin A supernatant in the presence or absence of the various peptides. Following 24 hours incubation, tritiated thymidine (1 μCi/well) was added overnight, with the cells harvested 18 hours later and CPM determined as noted above. ΔCPM and % inhibition of proliferation were calculated as follows:

$$\Delta CPM = CPM \text{ incorporated with stimulus } (GM\text{-}CSF \text{ or } IL\text{-}2) -$$

$$CPM \text{ incorporated without stimulus}$$

% inhibition of proliferation =

$$100 \times \frac{\Delta CPM \text{ w/o peptide} - \Delta CPM \text{ w/peptide}}{\Delta CPM \text{ w/o peptide}}$$

The results are shown in FIG. 9. Both the CDR I and CDR III peptides inhibit AML193 proliferation, while the CDR II peptides does not inhibit proliferation of this cell line. In contrast, the CDR I peptide has no effect on CTLL proliferation, and the CDR III peptide only inhibits CTLL growth at the highest concentration. These results indicate that the CDR I peptide (and perhaps the CDR III peptide) are specific antagonists of GM-CSF bioactivity.

Example 3

GM-CSF mediates it's activity by binding to specific cellular receptors (GM-CSFR) present on granulocyte and macrophage precursors, as well as mature phagocytic cells of both lineages. These receptors belong to a recently described supergene family and are potential targets for pharmacologic design. GM-CSF binding has been analyzed at a molecular level utilizing mutagenesis. Scanning-deletion analysis of murine GM-CSF indicated four regions critical for biological activity, spanning amino acids 18–22, 34–41, 52–61, and 94–115. Two disulfide bridges have been demonstrated between cysteines at positions 51–93, and 85–118. Of these, the disulfide bridge between 51–93 appears to be critical for maintaining structural integrity required for biological activity. One problem with deletion mutagenesis is the proclivity to induce alternations in molecular structure that do not affect the overall shape of the molecule are needed to map out regions critical for biological activity. Such studies have been performed, aided by the observation that murine GM-CSF is ineffective in stimulating human GM-CSFR bearing cells, while human GM-CSF is similarly incapable of affecting murine GM-CSF bearing cells. Comparative analysis of human versus murine GM-CSF indicates several regions of primary sequence divergence, with overall conservation of 78/144 residues, an additional 16 conservative substitutions, and a deletion. As the substitutions are scattered throughout the molecule, it was possible to swap regions of murine and human GM-CSF to locate sites critical for receptor interaction. These studies indicated a critical role for amino acids 21–31 and 77–94 in mediating the activity of human GM-CSF. Studies of large synthetic analogs of GM-CSF have implicated these helices as well. Recently the crystal structure of GM-CSF was elucidated, demonstrating the close proximity between portions of these regions.

To probe the potential importance of these sites in GM-CSF activity, short synthetic peptides were developed based on the sequences of human GM-CSF. The GM-CSF sequence was divided into 6 peptides ranging in size from 15–24 amino acids that spanned most of the molecule without overlap. Peptides are shown in Table 2. Four of the peptides incorporated the 4 separate alpha helices of the molecule (p029/p030, p3, p028, and p6) and one peptide incorporated the two reverse turns of the molecule (p5). Anti-sera was raised to these peptides in mice, and assayed for binding to GM-CSF and to the individual peptides by both ELISA and immunoprecipitation. In addition these antisera and the individual peptides were tested for efficacy in blocking GM-CSF—dependent cellular proliferation. The results of these studies support the role of the first alpha helix of GM-CSF in mediating GM-CSF biological activity.

MATERIALS AND METHODS

Peptide Design: The peptides used in these studies were designed based on simple structure analysis of native GM-CSF. For the peptides p029 and p030, a cysteine residue was added to either the amino or carboxy terminus to allow differential coupling to the p028.

Peptide Synthesis and Modification: All peptides were synthesized by solid-phase methods by the Wistar Institute peptide synthesis facility or Macromolecular Resources at Colorado State University, deprotected and released from the resin using anhydrous HF. Dimeric peptides were made by chemically linking p029 or p030 to p028 with the heterobifunctional cross-linking regent sulfo-MBS (Pierce Chemical Co.). This reagent has amine and sulfhydryl reactive moieties. This reagent targets primarily the side chain amino group of the lysine residue at position 8 of p028, allowing coupling to the cysteine residue on the amino terminus of p029 or the carboxy terminus of p030. To eliminate the sulfhydryl reactivity of p028, this peptide was first oxidized by stirring vigorously overnight a 2 mg/ml solution in 0.1 M $(NH_4)_2CO_3$, which reduced to <0.5% the free sulfhydryl groups available as assessed by Ellman determination (6,10). The peptides were then mixed with each other and sulfo-MBS in equimolar ratios at ≤1 mg/ml for the peptides, and stirred overnight in 0.1 M$(NH_4)_2CO_3$. The mixtures were dialyzed against distilled water (MW cutoff 1,000) and rotary evaporated under negative pressure. These conjugated peptides were used as unpurified mixtures. Thus, multiple conjugates were present in these mixtures along with unconjugated peptides. The only difference between p028–p029 and p028–p030 was the position of the cysteine residue. Peptides were lyophilized prior to use.

Coupling of Peptides to KLH and Immunization: Peptides were coupled using glutaraldehyde. Immunization of Balb/c mice was done using well known techniques. Serum was obtained following the 4th boost with antigen. Antisera from 3–5 animals was pooled for the assays performed.

Enzyme Linked Immunosorbent Assay (ELISA): ELISA was performed with polystyrene plates (Dynatech Laboratories, Inc.) coated with peptide or protein by evaporation of peptides (50 µg/ml) in distilled water overnight at 37° C., or with protein antigen (GM-CSF) by incubation of a 10 µg/ml solution in 0.1 M $NaHCO_3$ overnight at 4° C. The wells were washed with PBS, blocked with 0.05% Tween, 2% bovine serum albumin (BSA) in PBS and washed with PBS. Primary antibodies are added at varying dilutions for >1 hour at 37° C. After washing, secondary antibody, goat anti-mouse conjugated to horse radish peroxidase (HRP; Sigma Chemical Co., St. Louis, Mo.) was added per well in 1% BSA in PBS for 1–2 hours at 37° C. The substrate used for color development was 3,3',5,5'tetramethyl-benzidine dihydrochloride (TMB, Sigma Chemical Co.). The wells were decanted, washed extensively, and absorbance of samples was measured in a plate reader (MR 5000; Dynatech Laboratories) and expressed as OD 450 nm. Specific values were determined by subtracting the absorbance measured from uncoated wells from the absorbance to peptide/protein coated wells.

Immunoprecipitation: 5–25 µl of antisera was reacted with protein G beads (Sigma, St. Louis, Mo.) in eppendorf tubes and rotated overnight at 4° C. The tubes were centrifuged and the liquid aspirated. The beads were then washed 3X with lysis buffer (1% Triton, 0.05% SDS, 10 mM $Na_2HPO_4$–$NaH_2PO_4$, 150 mM NaCl, 5 mM EDTA, 100 µM $Na_3PO_4$ and 5 µg/ml Aprotinin all from Sigma) to remove unbound antibody. The beads were resuspended in 100 µl lysis buffer and $^{125}$I-GM-CSF was added to the tubes in the presence or absence of inhibitors (100 µl total volume) and rotated at 4° C. for one hour. The tubes were then centrifuged, the liquid discarded and the beads washed 3X. The beads were then resuspended in 2X sample buffer (0.5 M Tris HCl pH 6.8, 16% Glycerol, 3.2% SDS, 8% 2-ME and 0.04% Bromphenol Blue (all from Sigma) in distilled $H_2O$) and heated at 95° C. for 5 minutes to dissociate bonds. Samples were then loaded onto 10% SDS PAGE gels and analyzed by autoradiography.

Cell Lines & Proliferation Assay: AML 193 cells were obtained from the American Type Culture Collection (ATCC), and MO7E cells were from R. Zollner, Genetics Institute, (Cambridge Mass.). AML 193 grown serum free in Iscove's modified Dulbecco's media (IMDM) with insulin (10 µg/ml), transferrin (5–10 U/ml), 1% OPI media additive (oxalate, pyruvate & insulin), and GM-CSF 0.5 ng/ml. MO7E was grown in Dulbecco's modified Eagle's media (DMEM) with 10% heat inactivated FCS, Pen/strep, L-glutamine, and GM-CSF 0.5 ng/ml. KG1 and KG1a are grown in IMDM with 20% heat inactivated FCS, Pen/strep, and L-glutamine. For proliferation assays, $2\times10^4$ AML 193 or MO7E cells were cultured per well in 96 well round bottomed plates in the above media long with test antisera in a final volume of 200 µl. Following a 3–5 day incubation, tritiated thymidine (1 µCi/well) was added for an additional 18 hours, the cells harvested onto glass fiber filters utilizing a PhD cell harvester, and CPM incorporated determined in a standard liquid scintillation system.

RESULTS

Evaluation of Peptides and Antisera: Peptides encompassing the mature human GM-CSF molecule (excluding the carboxy terminus) were synthesized. Four of the peptides contained one complete alpha helical stretch. One of the alpha helices (representing amino acids 16–30) was represented by two separate peptides, p029 and p030, the only difference being a cysteine residue at either the carboxyl or amino terminus end. In addition, complexes were developed by chemically cross-linking p028 with either p029 or p030. The peptides were coupled to KLH and used to immunize mice. Each peptide elicited a good immune response. The antisera generated bound to the relevant peptide to which it was raised by both radioimmunoassay and ELISA with detectable binding at titers less than 1:10,000.

These anti-sera were then tested for binding to native GM-CSF by both ELISA and immunoprecipitation. By these assays, significant binding (>3 standard deviations above normal mouse serum control) of some of the anti-peptide antisera to GM-CSF is demonstrated. Anti-p029 and antisera to the complexed peptides (p028–029 and p028–030) displayed significant binding to GM-CSF by ELISA. Anti-p030 bound less well to the native GM-CSF, indicating that the position of the cysteine residue alters the immunogenic structure of this peptide compared with p029. Antiserum to p028 did not bind well in this assay. Significant binding of anti-p4 and anti-p5 to hGM-CSF by ELISA was observed. Anti-p6 bound less well, but still well over control values. Anti-p3 did not bind well in this assay.

These anti-sera were evaluated for their ability to immunoprecipitate $^{125}$I-GM-CSF. $^{125}$I-GM-CSF was immunoprecipitated by anti-p029 and anti-p028–029. This binding was also seen with anti-p4 and anti-p5 but again, as in the ELISA results, anti-p3 and anti-p6 exhibit markedly reduced binding to native GM-CSF. Thus in both solid-phase and liquid-phase assays, we demonstrated binding of specific anti-peptide antisera to the native hGM-CSF molecule. The specificity of binding was further demonstrated by the ability of the individual peptides to which these anti-sera were raised to inhibit immunoprecipitation. Anti-p029 binding to $^{125}$I-GM-CSF was blocked by p029, p030 and the conjugated peptides, but not by peptides representing other regions of the molecule. $^{125}$I-GM-CSF was immunoprecipitated by anti-pO28-030. Neither pO28 nor p3 inhibited this binding, reflecting the specificity of inhibition by the peptides p029, p030 and the conjugated peptides. Similar specificity was previously demonstrated on ELISA analysis of anti-p028–029 and anti-p028–030 binding to individual peptides, again demonstrating lack of reactivity with p028 but positive reactivity to p029 and p030. Thus, antisera to these conjugated peptides preferentially recognize the peptides corresponding to the first alpha helix of GM-CSF. The specificity of anti-p4 immunoprecipitation of $^{125}$I-GM-CSF by inhibition with p5 was observed. This data suggests that some of these linear peptides could assume conformations present in native human GM-CSF, and the antisera elicited were specific for the epitopes represented by the immunizing peptides.

Biological Effect of Anti-peptide Antisera: Anti-peptide anti-sera which showed binding of ELISA or on immunoprecipitation was tested for its ability to inhibit growth of two GM-CSF dependent cell lines, AML 193 and MO7E in five day assays. Since anti-p3 and anti-p028 could not be shown to bind to hGM-CSF, these anti-peptide anti-sera were not evaluated in these biologic assays. Varying dilutions of the antisera were added to the wells at the onset of the proliferation assay. The cells were stimulated with GM-CSF and proliferation measured by tritiated thymidine ($^3$H-TdR) incorporation. In the absence of GM-CSF, $^3$H-TdR incorporation into AML193 cells averaged less than 20,000 CPM incorporated while in the presence of GM-CSF, $^3$H-TdR incorporation averaged 80,000 CPM incorporated. The murine polyclonal anti-sera to hGM-CSF markedly inhibited the growth of these cells. The anti-peptide antisera, anti-p6, anti-p4, and anti-p029 inhibited proliferation at titers of 1:10 and 1:50, while anti-p5 had little effect. Inhibition of MO7E growth by anti- peptide antisera compared with polyclonal anti-GM-CSF was evaluated. Inhibition was observed for anti-p6, but not by anti-p4 or anti-p5. Similarly, inhibition was observed for anti-p029, at dilutions as high as 1:1000. Inhibition was also observed for anti-p028–029 and anti-p028–030. Both of these antisera bind to p029 or p030, not to p028. Thus, several of the antisera which significantly bound hGM-CSF were able to neutralize the growth of promoting effects of human GM-CSF. Of these, those recognizing the first alpha helix (p029) and the fourth alpha helix (p6), which are physically close in the native structure of GM-CSF, consistently inhibited the growth of two different GM-CSF dependent cell lines.

Biological effects of peptides: We next evaluated the ability of the peptides to inhibit growth of these GM-CSF dependent cell lines directly. The peptides were first evaluated for non-specific toxicity by assessing their effects on the growth of the human Jurkat T cell line. At the concentration used, p3 exhibited some non-specific inhibitory activity, and was therefore excluded from further analysis. At concentrations as high as 2 mg/ml, none of the other peptides exhibited non-specific toxicity. When tested on AML 193 or MO7E cells, consistent results were obtained with p029. At the high concentrations noted, both cell lines were inhibited by p029, representing the first alpha helix of GM-CSF. The peptides p4, p6, p030 and p028 were not inhibitory in these assays. The peptide p5 inhibited AML 193 growth, but not MO7E growth in these assays.

DISCUSSION

These studies utilized peptide design strategies to mimic portions of the GM-CSF molecule. The peptides were developed to assume the same predicted secondary studies as present in the native molecule. Prior studies from our group have succeeded in developing mimics of reverse turn structures and an alpha helix. The epitopes targeted in these studies were effective immunogens, and elicited high titered antisera to the immunizing peptides. The antisera against some of these peptides specifically bound GM-CSF, as demonstrated in both solid and liquid phase assays. While these assays do not measure the affinity of binding, they do indicate specific binding to the native molecule. This binding is site-specific since it can be inhibited by the individual peptides to which it was raised. As noted above, prior studies implicate two of these sites as potential contact regions for GM-CSF activity. However, specific recognition was only demonstrated by antisera to the first alpha helix-related active site (eg. anti-p029), while the second site peptide (p028) failed to elicit antisera which recognized native human GM-CSF.

In biologic assays, inhibition of hGM-CSF dependent cellular proliferation required high titer anti-sera. This was likely due to the moderate to low affinity of the anti-peptide antisera binding to GM-CSF. However, anti-p029, which represents the first alpha helix, and anti-p6, which represents the fourth alpha helix, inhibited proliferation of two GM-CSF dependent cell lines. These helices are closely situated in the GM-CSF crystal structure. The first alpha helix has been implicated in high affinity binding of GM-CSF to its receptor. Anti-p6 binds to a site structurally in close proximity to the first alpha helix, which suggests that steric inhibition of binding to the first alpha helix may occur. These data support the importance of the first alpha helix in mediating GM-CSF biological activity.

The other anti-peptide antisera tested did not consistently inhibit GM-CSF dependent cellular proliferation. Several potential artifactual interpretations of this data should be addressed. The ability of antisera to persist during the culture period without degradation is controlled for by the ability of murine anti-GM-CSF, anti-p029 and anti-p6 to inhibit the growth of these cells in the same assay. Thus, degradation of the antisera can be ruled out. A low affinity of the anti-sera—GM-CSF interaction may cause the antibodies to fall off during the protracted culture period. While this cannot be ruled out, anti-peptide antisera we have developed and tested similarly in other systems has not suffered from this problem. This includes similar binding on solid phase assays, and similar or more stringent assay conditions for "neutralization". It is possible that the anti-peptide antisera bound a portion of the peptide is a primary contact site.

Studies with the peptides themselves shows that high concentrations of p029 inhibits both MO7E and AML193 proliferation. This peptide did not inhibit growth of non-GM-CSF dependent cells, making non-specific toxicity unlikely. While we might assume that the observed inhibition is due to blocking GM-CSF—receptor interactions, additional studies assessing the ability of this peptide and analogs to block GM-CSF binding to specific receptors are needed to clarify the potential importance of these results. The high concentrations needed are likely due to the high free energy cost of the linear peptides assuming a bioactive conformation in solution.

These studies support the importance of the first alpha helix of GM-CSF in receptor interactions. Mutagenesis studies implicate this helix in binding of GM-CSF to the high affinity alpha/beta GM-CSF receptor, but not to the low affinity receptor (alpha chain alone). This is illustrated most strikingly by studies using mutants of residue Glu21 of GM-CSF. These mutants inhibit binding of GM-CSF to the low affinity receptor, but display little activity in inhibiting binding to the high affinity receptor. Based on these experiments, it has been proposed that the first alpha helix of GM-CSF is responsible for binding to the beta chain of the GM-CSF receptor.

TABLE 1

OLIGONUCLEOTIDE PRIMERS UTILIZED FOR PCR AND SEQUENCING

| DESIGNATION | CODONS | RESTRICTION SITE | SEQUENCE* | |
|---|---|---|---|---|
| 3315 | 1->7 | XbaI | CCCTCTAGAGACATTGTGCTGACCCAATCT | SEQ ID NO:6 |
| 5591** | 214->205 | EcoRI | ACAGAATTCCCTGTTGAAGCTCTAGACAAT | SEQ ID NO:7 |
| 931000** | 114->110 | — | CCAGTTGGTGCAGCATCA | SEQ ID NO:8 |
| pUC19 (3') | — | — | GTAAAACGACGGCCAGT | SEQ ID NO:9 |
| pDAB$_L$ (5') | 17->-10 | — | TTATTACTCGCTGCCCAACCAGCG | SEQ ID NO:10 |

*Single underline delineates restriction sites, double underline delineates added stop codon at 207.
**Antisense oligonucleotide. Note that 5591 introduces a stop codon at codon 207.

TABLE 2

Peptides Of Example 3

Peptide 028 (p028) Residues 78–99 (SEQ ID NO:11):
Thr Met Met Ala Ser His Tyr Lys Gln His Cys Pro Pro
Thr Pro Glu Thr Ser Cys Ala Thr Gln
Peptide 029 (p029) Residues 17–31 (SEQ ID NO:3):
(Cys) Asn Ala Ile Gln Glu Ala Arg Arg Leu Leu Asn Leu
Ser Arg Asp
Peptide 030 (p030) Residues 17–31 (SEQ ID NO:12):
Asn Ala Ile Gln Glu Ala Arg Arg Leu Leu Asn Leu Ser
Arg Asp (Cys)
Peptide 3 (p3) Residues 54–78 (SEQ ID NO:4):
Cys Leu Gln Thr Arg Leu Glu Leu Tyr Lys Gln Gly Leu
Arg Glu Ser Leu Thr Lys Gly Pro Leu Thr
Peptide 4 (p4) Residues 1–17 (SEQ ID NO:13):
Ala Pro Ala Arg Ser Pro Ser Pro Ser Thr Gln Pro Trp
Glu His Val Asn

TABLE 2-continued

Peptides Of Example 3

Peptide 5 (p5) Residues 31–54 (SEQ ID NO:14):
Thr Ala Ala Glu Met Asn Glu Thr Val Glu Val Ile Ser
Glu Met Phe Asp Leu Gln Glu Pro Thr Cys
Peptide 6 (p6) Residues 96–112 (SEQ ID NO:15):
Cys Ala Thr Gln Ile Ile Thr Phe Glu Ser Phe Lys Glu
Asn Leu Lys Asp

---

We claim:

1. A method of identifying a peptide having an amino acid sequence consisting of 15–25 amino acids, wherein said peptide mimics binding activity of a helix of an active region of a biologically active protein to its receptor in which an active region of said biologically active protein is a helix, said method comprising the steps of:

a) inoculating a first animal with an amount of a biologically active protein sufficient to invoke an immune response in said first animal which includes production of anti-biologically active protein antibodies by said first animal, wherein an active region of said biologically active protein is a helix;

b) isolating said anti-biologically active protein antibodies from said first animal;

c) inoculating a second animal with an amount of the isolated anti-biologically active protein antibodies sufficient to invoke an immune response which includes production by said second animal of antibodies which specifically bind to anti-biologically active protein antibodies;

d) isolating RNA from spleen cells from said second animal;

e) generating cDNA from said RNA;

f) amplifying fragments of said cDNA that encode antibody light chain regions including a complementarity determining region, and inserting said fragments into expression vectors to form recombinant expression vectors, wherein said expression vectors provide signal sequences to cDNA fragments for secretion of proteins encoded thereby;

g) transforming suitable host cells with said recombinant expression vectors to produce transformed host cells;

h) maintaining said transformed host cells under conditions which allow for expression of said fragments to produce proteins encoded thereby, wherein said proteins are secreted;

i) screening said proteins to identify a recombinant antibody light chain which competes with said biological active protein to bind with a neutralizing anti-biologically active protein monoclonal antibody;

j) identifying the amino acid sequences of complementarity determining regions of said recombinant antibody light chain which competes with said helix of an active region of a biological active protein to bind with said neutralizing anti-biologically active protein monoclonal antibody and k) synthesizing a peptide with an amino acid sequence that consists of between 15–25 amino acid residues and which comprises an amino acid sequence of a complementarity determining region of said recombinant antibody wherein said peptide mimics the binding activity of a helix of an active region of a biologically active protein to its receptor.

2. The method of claim 1 wherein said peptide has an amino acid sequence consisting of 20–21 amino acids.

3. The method of claim 1 wherein said peptide mimics binding activity of biologically active proteins selected from the group consisting of: IL-3, IL-5, growth hormone, M-CSF, G-CSF and IL-2.

4. The method of claim 1 wherein said first animal is a mouse.

5. The method of claim 1 wherein said anti-biologically active protein antibodies are anti-biologically active protein IgG antibodies isolated from sera from said first animal by affinity chromatography with sepharose-protein A.

6. The method of claim 1 wherein said second animal is a mouse.

7. The method of claim 1 wherein said expression vector is plasmid $pDAB_L$.

8. The method of claim 1 wherein said suitable host is *E. coli.*

9. The method of claim 1 wherein said synthesized peptide is conformationally restricted.

10. The method of claim 1 wherein said synthesized peptide is dimerized.

11. The method of claim 1 wherein said peptide has an amino acid sequence consisting of 15–22 amino acids.

12. The method of claim 1 wherein said peptide has an amino acid sequence consisting of 19–23 amino acids.

13. The method of claim 1 wherein said peptide has an amino acid sequence consisting of 17–21 amino acids.

* * * * *

UNITED STATES PATENT AND TRADEMARK OFFICE
CERTIFICATE OF CORRECTION

PATENT NO. : 5,837,460
DATED : November 17, 1998
INVENTOR(S) : Joan M. Von Feldt et al It is certified that error appears in the above-identified patent and that said Letters Patent is hereby corrected as shown below:

Col. 15, line 50, "PDABL" should be --$pDAB_L$--

Signed and Sealed this

Thirtieth Day of March, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

Cys Arg Ala Ser Lys Ser Val Ser Ser Ser Gly Tyr Ser Tyr Met His
1               5                   10                  15

Trp Tyr Gln Gln
            20

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Cys Gln His Ser Arg Glu Leu Pro Trp Thr Phe Gly Gly Gly Thr Arg
1               5                   10                  15

Leu Glu Ile Lys Arg
            20

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Cys Asn Ala Ile Gln Glu Ala Arg Arg Leu Leu Asn Leu Ser Arg Asp
1               5                   10                  15

( 2 ) INFORMATION FOR SEQ ID NO:4:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Cys Leu Gln Thr Arg Leu Glu Leu Tyr Lys Gln Gly Leu Arg Glu Ser
1               5                   10                  15

Leu Thr Lys Gly Pro Leu Thr
            20

( 2 ) INFORMATION FOR SEQ ID NO:5:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Tyr Leu Ala Ser Asn Leu Glu Ser Gly Val Pro Pro Arg Phe Ser Gly
1               5                   10                  15

Ser ( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CCCTCTAGAG ACATTGTGCT GACCCAATCT				30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:7:

ACAGAATTCC CTGTTGAAGC TCTAGACAAT                    30

( 2 ) INFORMATION FOR SEQ ID NO:8:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:8:

CCAGTTGGTG CAGCATCA                                 18

( 2 ) INFORMATION FOR SEQ ID NO:9:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:9:

GTAAA ACGAC GGCCA GT                                17

( 2 ) INFORMATION FOR SEQ ID NO:10:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:10:

TTATTACTCG CTGCCCAACC AGCG                          24

( 2 ) INFORMATION FOR SEQ ID NO:11:

( i ) SEQUENCE CHARACTERISTICS:
                ( A ) LENGTH: 22 amino acids
                ( B ) TYPE: amino acid
                ( D ) TOPOLOGY: linear ( i i ) MOLECULE TYPE: protein ( x i ) SEQUENCE DESCRIPTION: SEQ ID NO:11:

Thr Met Met Ala Ser His Tyr Lys Gln His Cys Pro Pro Thr Pro Glu
1               5                   10                  15
Thr Ser Cys Ala Thr Gln
            20

( 2 ) INFORMATION FOR SEQ ID NO:12:

( i ) SEQUENCE CHARACTERISTICS:
                ( A ) LENGTH: 16 amino acids
                ( B ) TYPE: amino acid
                ( D ) TOPOLOGY: linear ( i i ) MOLECULE TYPE: protein ( x i ) SEQUENCE DESCRIPTION: SEQ ID NO:12:

Asn Ala Ile Gln Glu Ala Arg Arg Leu Leu Asn Leu Ser Arg Asp Cys
1               5                   10                  15

( 2 ) INFORMATION FOR SEQ ID NO:13:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

Ala Pro Ala Arg Ser Pro Ser Pro Ser Thr Gln Pro Trp Glu His Val
1               5                   10                  15

Asn ( 2 ) INFORMATION FOR SEQ ID NO:14:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Thr Ala Ala Glu Met Asn Glu Thr Val Glu Val Ile Ser Glu Met Phe
1               5                   10                  15

Asp Leu Gln Glu Pro Thr Cys
                20

( 2 ) INFORMATION FOR SEQ ID NO:15:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

Cys Ala Thr Gln Ile Ile Thr Phe Glu Ser Phe Lys Glu Asn Leu Lys
1               5                   10                  15

Asp